(12) United States Patent
Smaby et al.

(10) Patent No.: US 10,595,836 B2
(45) Date of Patent: Mar. 24, 2020

(54) SYSTEMS AND METHODS FOR CONFIRMING DISC ENGAGEMENT

(71) Applicant: Intuitive Surgical Operations, Inc., Sunnyvale, CA (US)

(72) Inventors: Niels Smaby, Palo Alto, CA (US); Gregory W. Dachs, II, San Mateo, CA (US); Bruce M. Schena, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 235 days.

(21) Appl. No.: 15/126,061

(22) PCT Filed: Mar. 17, 2015

(86) PCT No.: PCT/US2015/021111
§ 371 (c)(1),
(2) Date: Sep. 14, 2016

(87) PCT Pub. No.: WO2015/142958
PCT Pub. Date: Sep. 24, 2015

(65) Prior Publication Data
US 2017/0172549 A1    Jun. 22, 2017

Related U.S. Application Data

(60) Provisional application No. 61/954,408, filed on Mar. 17, 2014, provisional application No. 61/954,571, (Continued)

(51) Int. Cl.
*A61B 34/30* (2016.01)
*A61B 17/00* (2006.01)
(Continued)

(52) U.S. Cl.
CPC .............. *A61B 17/00* (2013.01); *A61B 34/35* (2016.02); *A61B 34/71* (2016.02);
(Continued)

(58) Field of Classification Search
CPC ................................ A61B 50/13; A61B 10/02
See application file for complete search history.

(56) References Cited

U.S. PATENT DOCUMENTS

| 4,542,272 A | 9/1985 | Hubbard et al. |
| 5,214,573 A | 5/1993 | Roza |

(Continued)

FOREIGN PATENT DOCUMENTS

| CN | 101297267 A | 10/2008 |
| CN | 101443162 A | 5/2009 |

(Continued)

OTHER PUBLICATIONS

Extended European Search Report for Application No. 15765493.0, dated Jul. 28, 2017, 7 pages.
(Continued)

*Primary Examiner* — Bickey Dhakal
*Assistant Examiner* — Charles S Laughlin
(74) *Attorney, Agent, or Firm* — Haynes and Boone, LLP

(57) ABSTRACT

A method comprising receiving an input coupling adjacent to a drive input driven by an actuating element, the input coupling being coupled to a joint output and the joint output being connected to a movable object. The method further comprising rotating the actuating element to drive the drive input and determining, by a control system, whether a resistance torque greater than an inherent drivetrain resistance torque is experienced by the actuating element. The inherent drivetrain resistance torque is for a drivetrain including the input coupling, the drive input, and the joint output. The method also includes determining, by the control system, whether the drive input has engaged the input coupling based on the determination that the resistance torque greater than the inherent drivetrain resistance torque has been experienced by the actuating element.

20 Claims, 16 Drawing Sheets

Related U.S. Application Data filed on Mar. 17, 2014, provisional application No. 62/103,991, filed on Jan. 15, 2015.

(51) Int. Cl.
*A61B 34/00* (2016.01)
*A61B 34/35* (2016.01)
*A61B 90/00* (2016.01)

(52) U.S. Cl.
CPC .............. *A61B 2017/00464* (2013.01); *A61B 2034/302* (2016.02); *A61B 2090/066* (2016.02); *A61B 2090/0812* (2016.02)

(56) References Cited

U.S. PATENT DOCUMENTS

| | | | |
|---|---|---|---|
| 5,679,423 A | 10/1997 | Shah | |
| 5,803,086 A | 9/1998 | Scholz et al. | |
| 6,331,181 B1 | 12/2001 | Tierney et al. | |
| 6,471,172 B1 | 10/2002 | Lemke et al. | |
| 7,096,870 B2 | 8/2006 | Lamprich et al. | |
| 7,125,403 B2 | 10/2006 | Julian et al. | |
| 7,758,569 B2 | 7/2010 | Brock | |
| 7,947,050 B2 | 5/2011 | Lee et al. | |
| 7,963,913 B2 | 6/2011 | Devengenzo et al. | |
| 8,220,468 B2 | 7/2012 | Cooper et al. | |
| 8,506,555 B2 | 8/2013 | Ruiz | |
| 8,529,582 B2 | 9/2013 | Devengenzo et al. | |
| 8,555,892 B2 | 10/2013 | Traub | |
| 9,687,312 B2 | 6/2017 | Dachs, II et al. | |
| 9,839,487 B2 | 12/2017 | Dachs, II et al. | |
| 10,022,193 B2 | 7/2018 | Cooper et al. | |
| 10,045,828 B2 | 8/2018 | Dachs, II et al. | |
| 10,213,268 B2 | 2/2019 | Dachs, II et al. | |
| 10,278,784 B2 | 5/2019 | Dachs, II | |
| 2002/0032452 A1 | 3/2002 | Tierney et al. | |
| 2002/0111635 A1 | 8/2002 | Jensen et al. | |
| 2003/0216723 A1 | 11/2003 | Shinmura et al. | |
| 2004/0049205 A1* | 3/2004 | Lee ............... | A61B 34/71 606/130 |
| 2005/0240178 A1 | 10/2005 | Morley et al. | |
| 2005/0244217 A1 | 11/2005 | Burke et al. | |
| 2006/0235436 A1 | 10/2006 | Anderson et al. | |
| 2006/0260622 A1 | 11/2006 | Wooley et al. | |
| 2007/0119274 A1 | 5/2007 | Devengenzo et al. | |
| 2007/0142971 A1 | 6/2007 | Schena et al. | |
| 2008/0103491 A1 | 5/2008 | Omori et al. | |
| 2008/0140088 A1* | 6/2008 | Orban, III ............... | A61B 34/30 606/130 |
| 2010/0163057 A1 | 7/2010 | Anderson et al. | |
| 2010/0170519 A1 | 7/2010 | Romo et al. | |
| 2010/0175701 A1 | 7/2010 | Reis et al. | |
| 2010/0234857 A1 | 9/2010 | Itkowitz et al. | |
| 2011/0015650 A1 | 1/2011 | Choi et al. | |
| 2011/0084113 A1 | 4/2011 | Bedi et al. | |
| 2011/0118754 A1 | 5/2011 | Dachs, II et al. | |
| 2011/0213383 A1 | 9/2011 | Lee et al. | |
| 2011/0277776 A1 | 11/2011 | McGrogan et al. | |
| 2011/0288560 A1 | 11/2011 | Shohat et al. | |
| 2011/0290854 A1 | 12/2011 | Timm et al. | |
| 2011/0290855 A1 | 12/2011 | Moore et al. | |
| 2011/0295270 A1 | 12/2011 | Giordano et al. | |
| 2011/0313477 A1 | 12/2011 | McLean et al. | |
| 2012/0197094 A1 | 8/2012 | Zhang et al. | |
| 2012/0239060 A1 | 9/2012 | Orban, III | |
| 2012/0247489 A1 | 10/2012 | Orban, III et al. | |
| 2012/0292367 A1 | 11/2012 | Morgan et al. | |
| 2013/0110129 A1 | 5/2013 | Reid et al. | |
| 2013/0211397 A1 | 8/2013 | Parihar et al. | |
| 2013/0211401 A1 | 8/2013 | Bailey et al. | |
| 2013/0274062 A1 | 10/2013 | Arai et al. | |
| 2013/0274657 A1 | 10/2013 | Zirps et al. | |
| 2013/0325034 A1* | 12/2013 | Schena ................. | A61B 34/30 606/130 |
| 2013/0331858 A1 | 12/2013 | Devengenzo et al. | |
| 2014/0001234 A1 | 1/2014 | Shelton, IV et al. | |
| 2014/0066944 A1 | 3/2014 | Taylor et al. | |
| 2014/0069437 A1 | 3/2014 | Reis et al. | |
| 2015/0223832 A1 | 8/2015 | Swaney et al. | |
| 2015/0257841 A1 | 9/2015 | Dachs, II | |
| 2015/0257842 A1 | 9/2015 | Dachs, II | |
| 2016/0184037 A1 | 6/2016 | Cooper et al. | |
| 2016/0354173 A1 | 12/2016 | Dachs, II et al. | |
| 2016/0361049 A1 | 12/2016 | Dachs, II et al. | |
| 2016/0361124 A1 | 12/2016 | Dachs, II et al. | |
| 2016/0361126 A1 | 12/2016 | Schena et al. | |
| 2016/0361127 A1 | 12/2016 | Dachs, II et al. | |
| 2016/0361129 A1 | 12/2016 | Morrissette et al. | |
| 2016/0361131 A1 | 12/2016 | Dachs, II et al. | |
| 2016/0367328 A1 | 12/2016 | Dachs, II et al. | |
| 2017/0273752 A1 | 9/2017 | Dachs, II et al. | |
| 2018/0064501 A1 | 3/2018 | Dachs, II | |
| 2018/0168752 A1 | 6/2018 | Scheib et al. | |
| 2018/0344419 A1 | 12/2018 | Dachs, II et al. | |
| 2019/0183596 A1 | 6/2019 | Dachs, II | |

FOREIGN PATENT DOCUMENTS

| | | |
|---|---|---|
| CN | 102630154 A | 8/2012 |
| DE | 102012008535 A1 | 10/2013 |
| DE | 102012013242 A1 | 1/2014 |
| EP | 1862123 A2 | 12/2007 |
| EP | 2259744 A1 | 12/2010 |
| GB | 2538326 A | 11/2016 |
| JP | H0666326 A | 3/1994 |
| KR | 20110032444 A | 3/2011 |
| KR | 20110036452 A | 4/2011 |
| KR | 20110095795 A | 8/2011 |
| KR | 20130080638 A | 7/2013 |
| KR | 20130120316 A | 11/2013 |
| WO | WO-2007075864 A1 | 7/2007 |
| WO | WO-2007095637 A1 | 8/2007 |
| WO | WO-2007126443 A2 | 11/2007 |
| WO | WO-2009151205 A1 | 12/2009 |
| WO | WO-2010126128 A1 | 11/2010 |
| WO | WO-2011037394 A2 | 3/2011 |
| WO | WO-2011143016 A1 | 11/2011 |
| WO | WO-2013018931 A1 | 2/2013 |
| WO | WO-2013181536 A1 | 12/2013 |
| WO | WO-2014035803 A1 | 3/2014 |
| WO | WO-2015142824 A1 | 9/2015 |

OTHER PUBLICATIONS

Extended European Search Report for Application No. 15765779.2, dated Jul. 18, 2017, 8 pages.
Extended European Search Report for Application No. EP15764089.7, dated Oct. 25, 2017, 11 pages.
Extended European Search Report for Application No. EP15764268.7, dated Nov. 6, 2017, 8 pages.
Extended European Search Report for Application No. EP15764745.4, dated Oct. 30, 2017, 10 pages.
Extended European Search Report for Application No. EP15764940.1, dated Oct. 30, 2017, 8 pages.
Extended European Search Report for Application No. 15766019.2, dated Oct. 20, 2017, 7 pages.
International Search Report and Written Opinion for Application No. PCT/US15/21111, dated May 21, 2015, 10 pages.
International Search Report and Written Opinion for Application No. PCT/US15/20880, dated Jul. 14, 2015, 9 pages.
International Search Report and Written Opinion for Application No. PCT/US15/20882, dated May 29, 2015, 14 pages.
International Search Report and Written Opinion for Application No. PCT/US15/20884, dated Jun. 12, 2015, 13 pages.
International Search Report and Written Opinion for Application No. PCT/US15/20886, dated Jun. 4, 2015, 19 pages.
International Search Report and Written Opinion for Application No. PCT/US15/20876, dated Jun. 12, 2015, 17 pages.
International Search Report and Written Opinion for Application No. PCT/US15/20885, dated Jun. 5, 2015, 7 pages.

(56) References Cited

OTHER PUBLICATIONS

International Search Report and Written Opinion for Application No. PCT/US15/20888, dated Jun. 5, 2015, 9 pages.
International Search Report and Written Opinion for Application No. PCT/US15/21020, dated Jun. 5, 2015, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP15764610.0, dated Nov. 23, 2017, 8 pages.
Extended European Search Report for Application No. EP15764881.7, dated Nov. 30, 2017, 10 pages.
Extended European Search Report for Application No, 19181058.9 dated Aug. 22, 2019, 7 pages.

* cited by examiner

SYSTEMS AND METHODS FOR CONFIRMING DISC ENGAGEMENT

PRIORITY

This patent application claims priority to and the benefit of the filing date of U.S. Provisional Patent Application 61/954,408, titled "Systems and Methods for Confirming Disc Engagement," filed Mar. 17, 2014, and U.S. Provisional Patent Application 62/103,991, titled "Coupler to Transfer Motion to Surgical Instrument From Teleoperated Actuator," filed Jan. 15, 2015, and U.S. Provisional Patent Application 61/954,571, titled "Coupler to Transfer Motion to Surgical Instrument From Servo Actuator," filed Mar. 17, 2014, which are all incorporated by reference herein in their entirety.

FIELD

The present disclosure is directed to systems and methods for mechanical engagement, and more particularly to systems and methods for confirming that a drive coupling has successfully engaged with an input coupling.

BACKGROUND

Many mechanical systems make use of motors that move objects into different positions. In general, an actuating element, such as a motor, has a drive input that mates with an input coupling of a tool to be actuated. Various mechanical structures may be used to engage the drive input with the input coupling. One example is a boss and pocket structure. Specifically, the drive input may include a disc that has a boss extending from the surface of the disc. The boss may be designed to fit into a corresponding pocket on a disc connected to the input coupling. When the boss is successfully positioned within the pocket, rotation of the drive input causes rotation of the input coupling, which in turn causes movement of the tool.

A mechanical system that involves engaging a drive input with an input coupling may be a teleoperative medical system. The teleoperative medical system may include motors with drive inputs that couple to and operate interchangeable medical instruments. In some embodiments, the drive inputs of the motors include drive discs that engage with corresponding instrument discs on the medical instrument. Each of the instrument discs may actuate a different type of motion in the medical instrument. For example, one disc may control actuating members that change the roll position of the instrument. Other discs may control actuating members that change the yaw, pitch, or grip of the medical instrument. When an interchangeable instrument is connected to the teleoperative medical system, each of the drive discs on the arm must be appropriately engaged with the instrument discs so that the actuating elements will drive movement of the medical instrument as desired.

When the instrument discs are first placed against the drive discs of the motors, the instrument discs may not be precisely aligned with the drive discs. The drive discs may be rotated until they fall into the corresponding pockets of the instrument discs. In some cases, the bosses may not engage the pockets properly on the first rotational pass, but may engage properly on a subsequent rotational pass. Before a medical procedure may be performed, confirmation that the drive discs have appropriately engaged the instrument discs is needed.

SUMMARY

The embodiments of the invention are summarized by the claims that follow below.

In one embodiment, a method comprises receiving an input coupling adjacent to a drive input, the drive input being driven by an actuating element, the input coupling being coupled to a joint output, the joint output being connected to a movable object. The method further comprises rotating the actuating element until a resistance torque is experienced by the actuating element and determining, based upon the resistance torque, whether the drive input has engaged the input coupling.

In another embodiment, a system includes a medical instrument including an input coupling and an actuatable instrument tip, the input coupling configured to move the actuatable instrument tip. The system further includes an instrument carriage including a drive coupling configured to engage the input coupling and a motor coupled to rotate the drive coupling and a control system configured to rotate the motor until a commanded motion trajectory is completed or a resistance torque is experienced by the motor and determine, based upon a magnitude of the resistance torque, whether the drive coupling has engaged the input coupling.

In another embodiment, a method for confirming instrument engagement includes receiving a plurality of instrument discs to a plurality of drive discs, wherein at least two of the plurality of instrument discs coordinate to move an instrument tip along a degree of freedom, with actuating elements connected to the drive discs, driving the discs until motion of the discs has stalled, determine a torque resistance experienced by each of the drive discs, and determine if engagement of the drive discs was successful based on the torque resistances.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
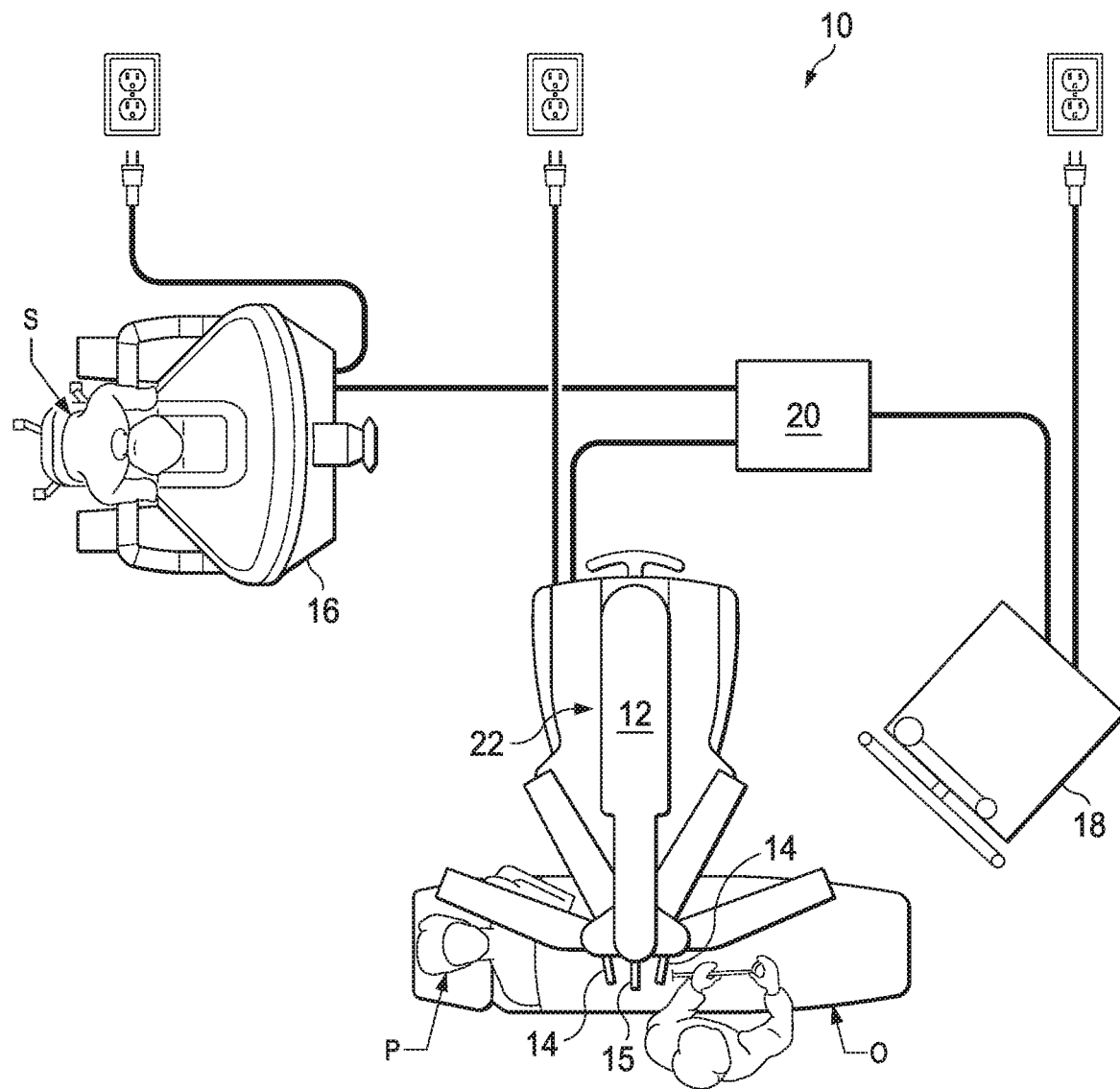
FIG. 1A is a plan view of a minimally invasive teleoperative medical system being used to perform a surgery, in accordance with many embodiments.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s)

may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 1B:
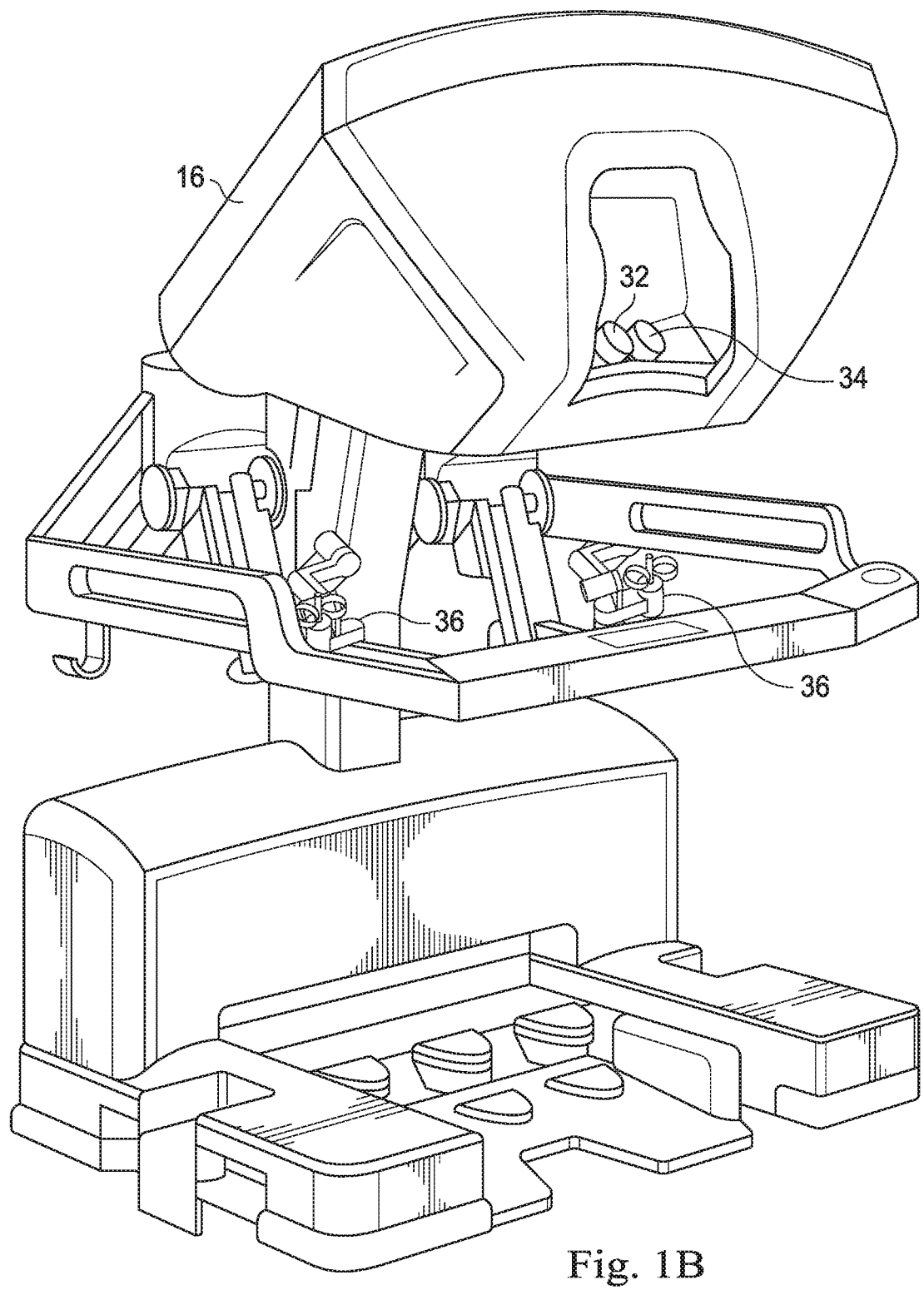
FIG. 1B is a perspective view of a surgeon's control console for a teleoperative medical system, in accordance with many embodiments.

FIG. 1B is a perspective view of the surgeon's console 16. The surgeon's console 16 includes a left eye display 32 and a right eye display 34 for presenting the surgeon S with a coordinated stereo view of the surgical site that enables depth perception. The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36.

Figure 1C:
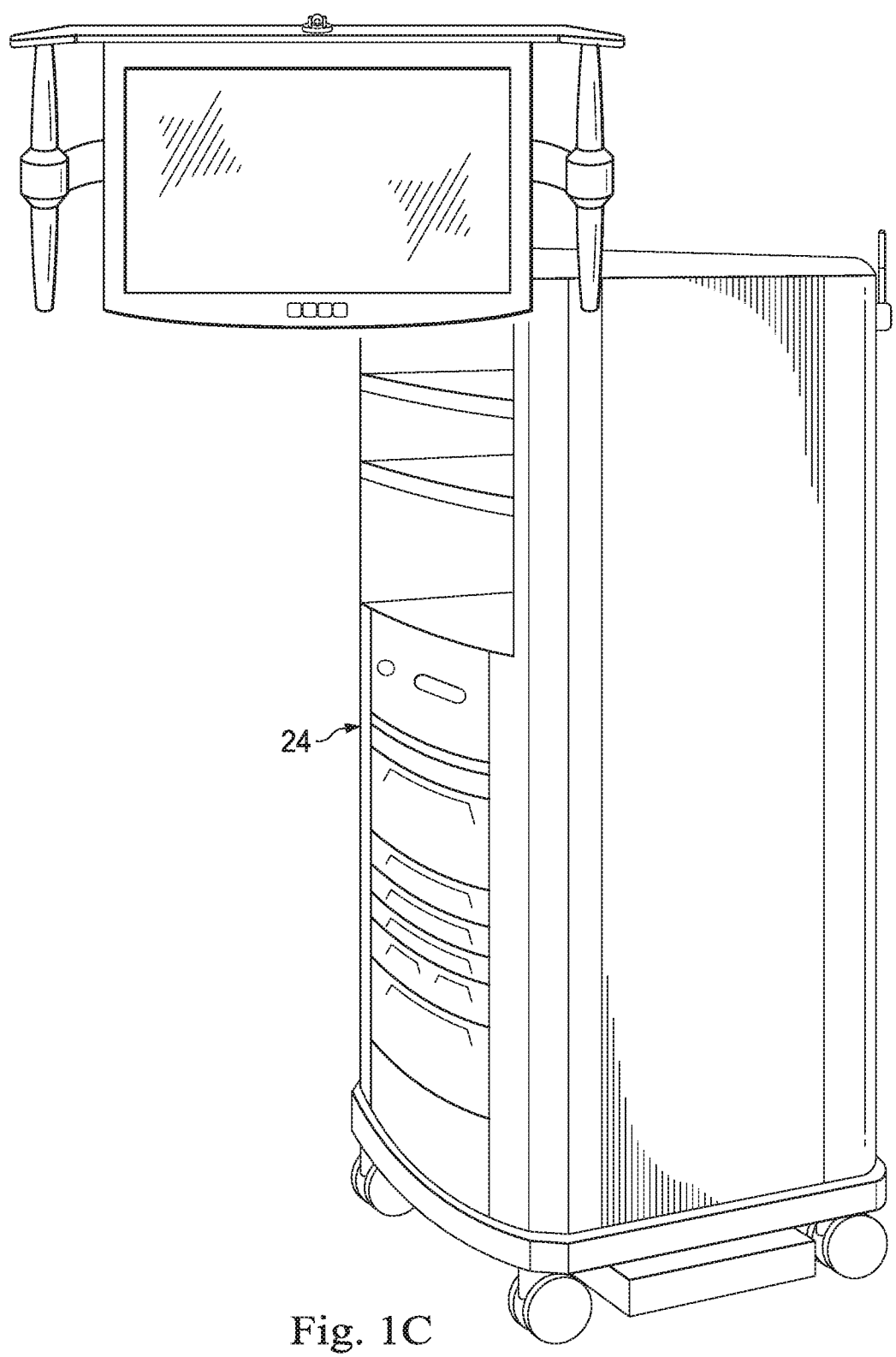
FIG. 1C is a perspective view of a teleoperative medical system electronics cart, in accordance with many embodiments.

FIG. 1C is a perspective view of the electronics cart 18. The electronics cart 18 can be coupled with the endoscope 15 and can include a processor to process captured images for subsequent display, such as to a surgeon on the surgeon's console, or on another suitable display located locally and/or remotely. For example, where a stereoscopic endoscope is used, the electronics cart 18 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The electronics cart 18 may also include a display monitor and components of the control system 20.

Figure 1D:
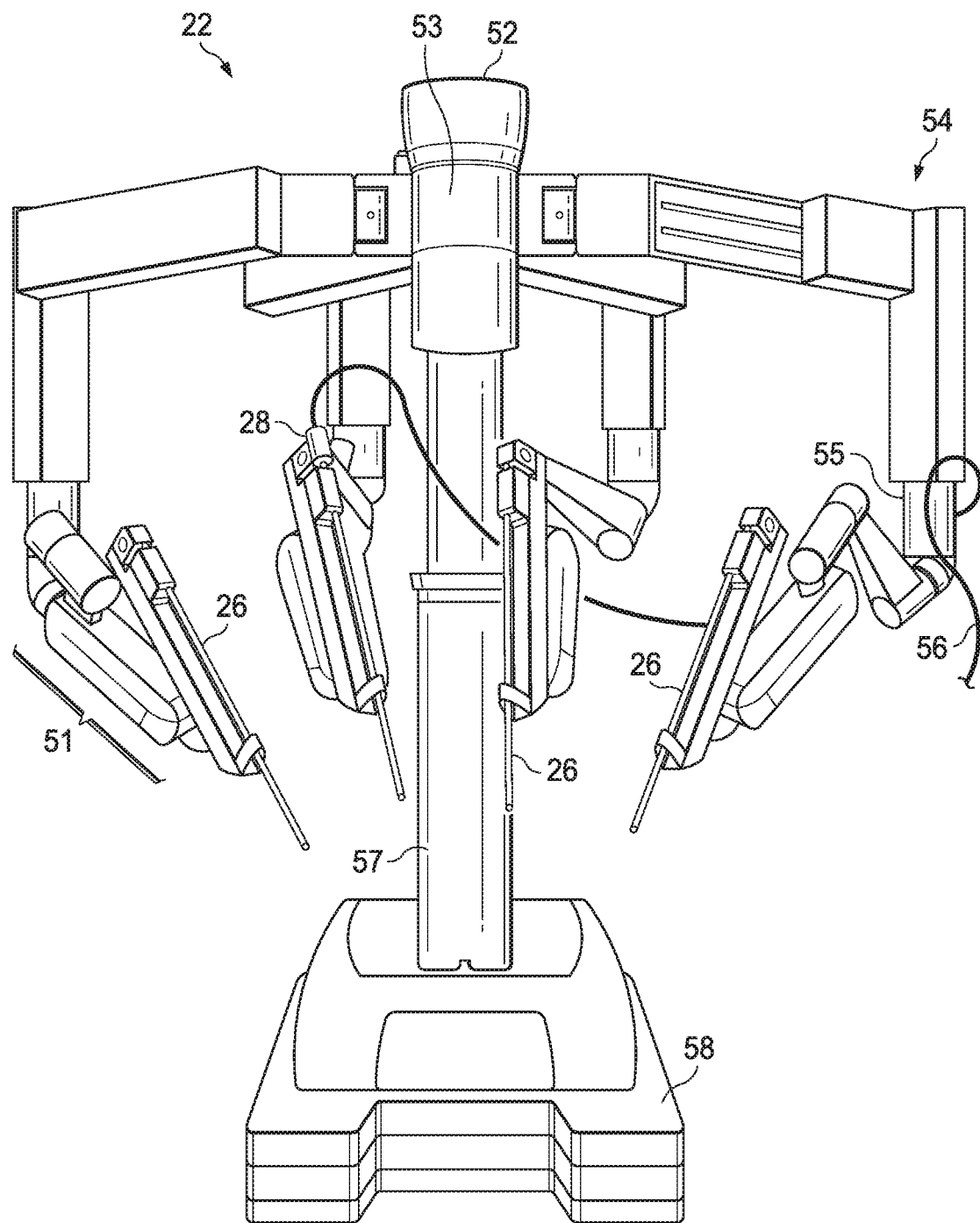
FIG. 1D is a perspective view of a patient side cart, according to one example of principles described herein.

FIG. 1D is a perspective view of one embodiment of a teleoperational assembly 12 which may be referred to as a patient side cart. The patient side cart 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 22 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 22 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon 18 begins operation with the teleoperative components.

Figure 1E:
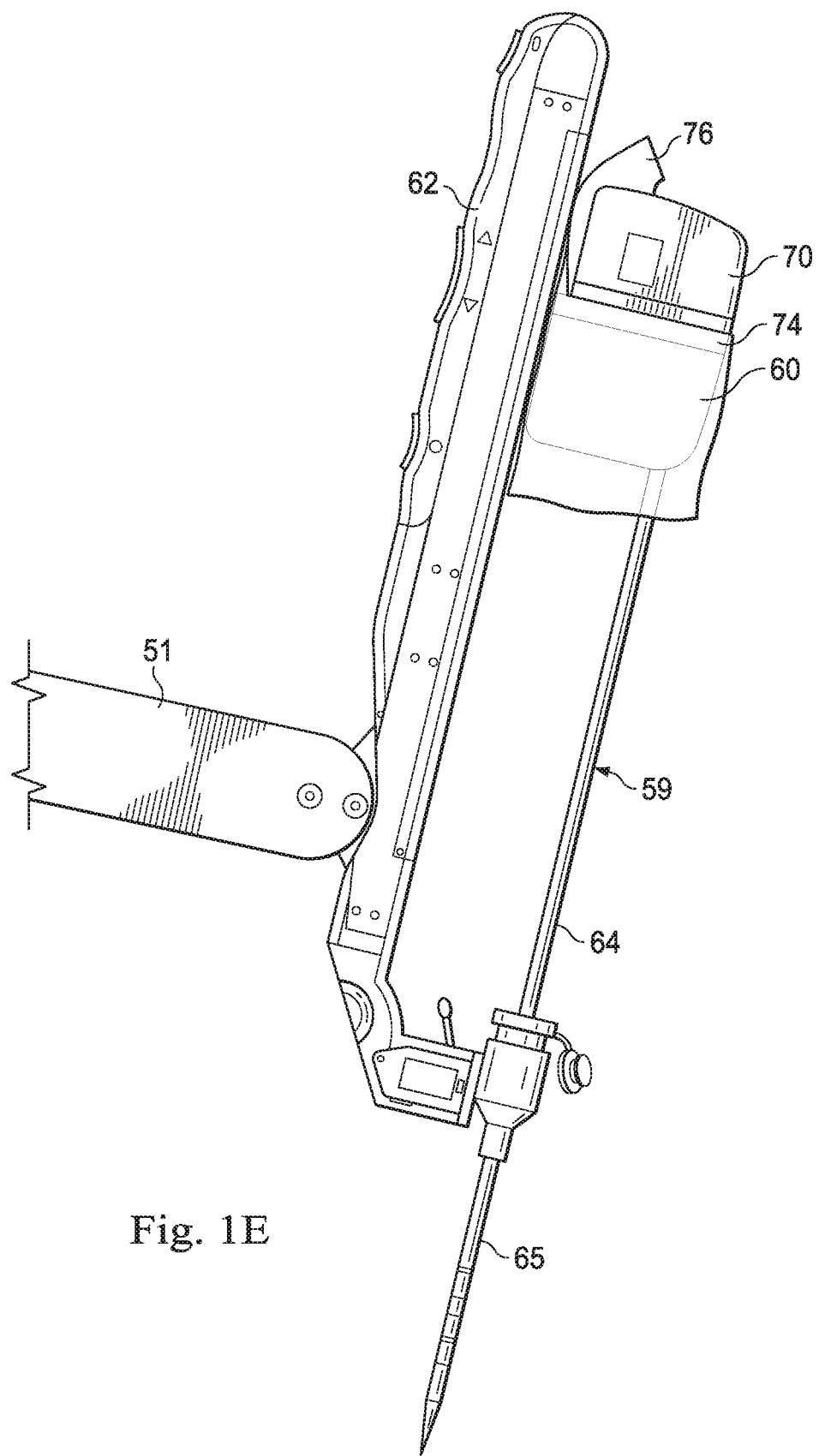
FIG. 1E illustrates a portion of a manipulator arm coupled to an instrument.
Figure 1F:
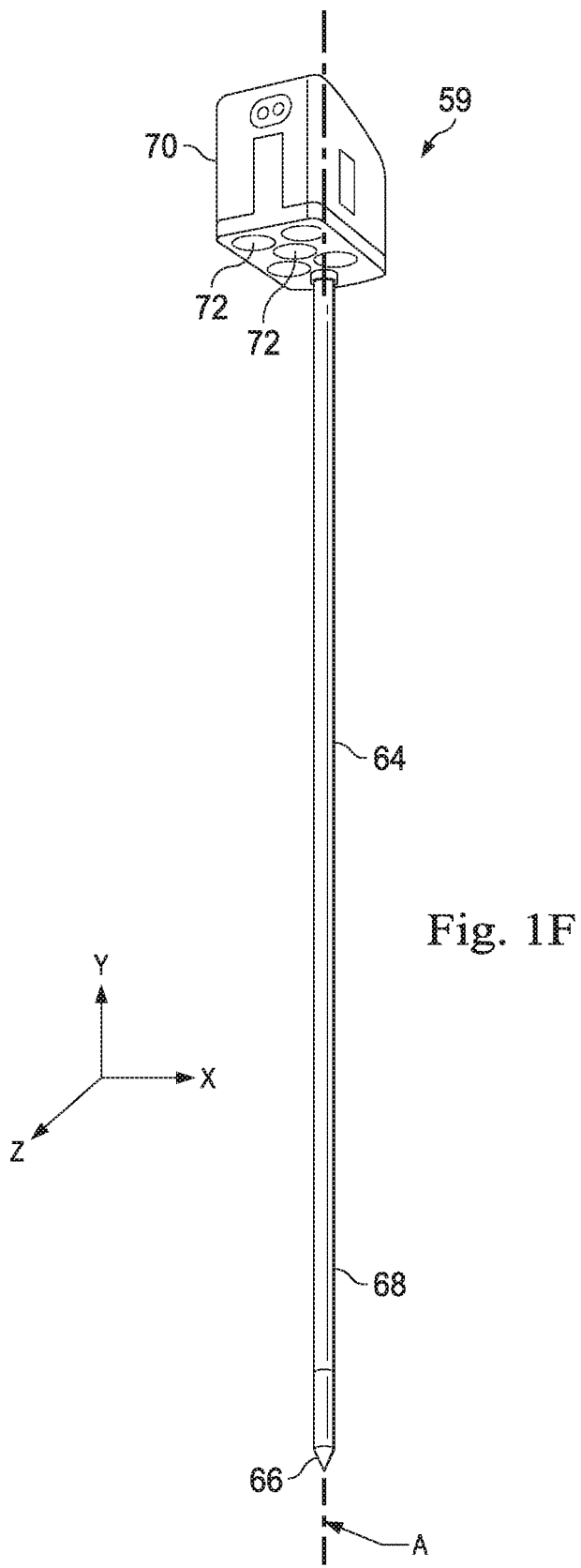
FIG. 1F illustrates the instrument of FIG. 1E in greater detail.

FIG. 1E illustrates a portion of the manipulator arm 51 coupled to an instrument 59 (e.g., an instrument 14). An instrument carriage 60 travels linearly along an instrument spar 62. As shown also in FIG. 1F, the instrument 59 includes an instrument shaft 64, an instrument tip 66, a wrist joint 68, and an instrument body 70. The instrument body 70 includes instrument discs 72 that couple to actuating members that extend through the shaft 64 to actuate the wrist joint 68 and the tip 66. A cannula 65 is coupled to a distal end of the instrument spar 62 and is sized to receive the shaft 64. The instrument carriage 60 houses motors for driving movement of respective drive discs. In one embodiment, for example, the carriage may house five motors that activate five drive discs to transmit motion to the instrument discs 72 when coupled. The carriage may, however, include any number of motors and corresponding drive discs. A sterile adaptor 74 is coupled to a sterile drape 76. The sterile adaptor 74 includes passive adaptor discs that couple on one side to the drive discs of the carriage and on an opposite side to the instrument discs 72. When the instrument discs 72 are coupled to the drive discs via the adaptor discs, the motors of the carriage 60 may be operated to effect motion of the instrument 59. For example, the shaft 64, wrist 68, and tip 66 may be rotated about a longitudinal axis A of the shaft. Also for example, the wrist 68 may be actuated to move the tip 66 in a pitch motion about an X-direction axis or a yaw motion about a Z-direction axis. In various alternatives, the sterile adaptor may be omitted and the drive discs may directly engage the instrument discs.

Figure 2A:
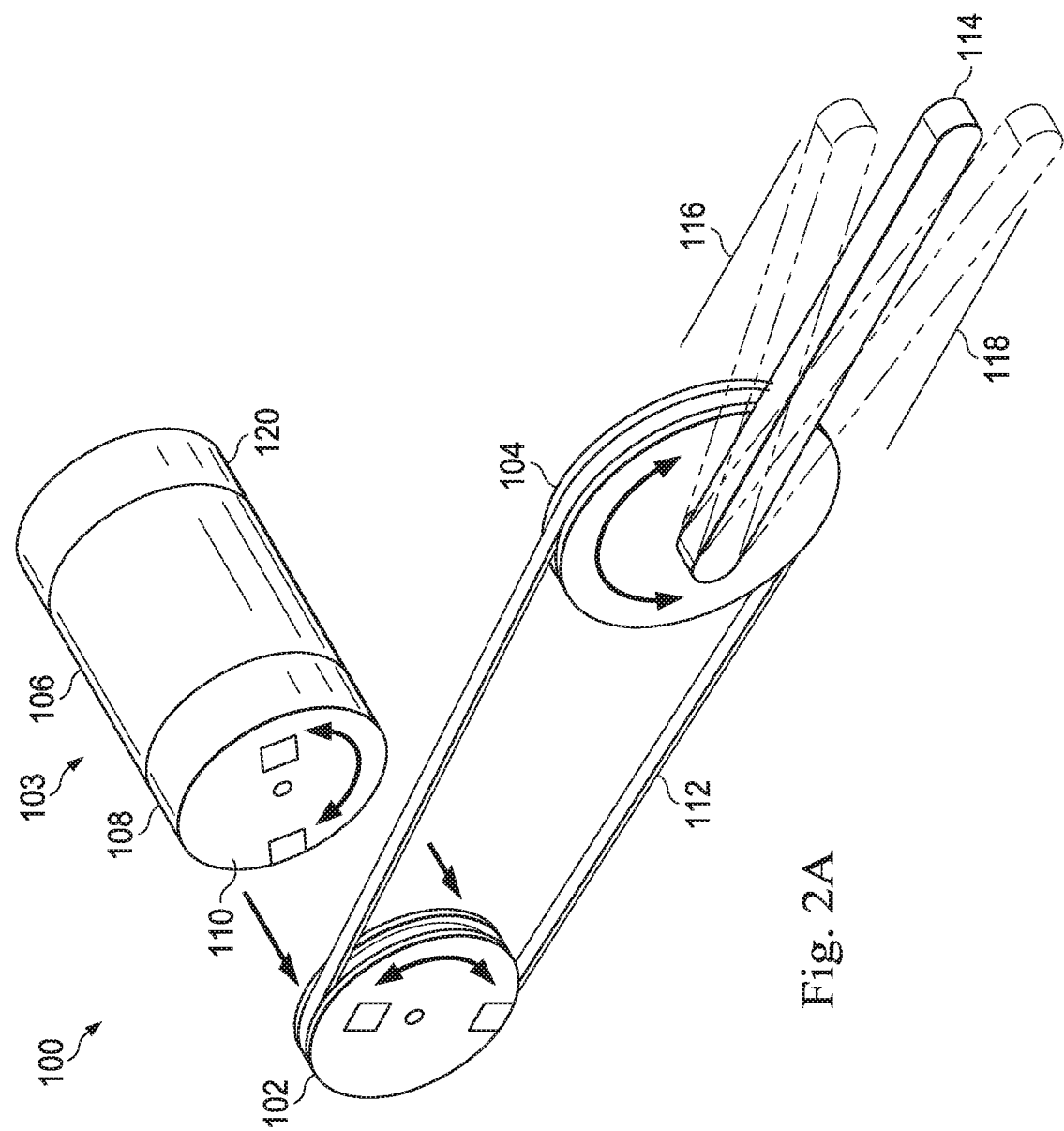
FIG. 2A is a diagram showing an illustrative system for engaging a drive disc to an instrument disc that is coupled to a joint output, according to one example of principles described herein.

FIG. 2A is a diagram showing an illustrative system 100 for engaging a drive disc 110 (e.g., a drive disc of the carriage 60) to an instrument disc 102 (e.g., an instrument disc 72) that is coupled to a joint output 104 (e.g., the wrist joint 68). According to the present example, an actuating element 103 includes an actuator 106, a gearbox 108, and the drive disc 110. The actuator 106 is connected to the gearbox 108. The gearbox 108 is coupled with the drive disc 110. The drive disc 110 is configured to engage the instrument disc 102. The instrument disc 102 is coupled to the joint output 104 through an actuation system 112. While the system 112 is illustrated as a pulley, the system 112 may be a set of gears, cables, drive rods, or other actuating members coupling the instrument disc 102 to the joint output 104. The joint output 104 is configured to move a manipulatable object 114 (e.g., the tip 66). In various alternative embodiments, an adaptor disc may be coupled between the drive disc 110 and the instrument disc 102. Therefore, in the various engagement procedures and embodiments disclosed herein, the instrument discs may, alternatively, engage with adaptor discs instead of directly with drive discs. Thus, all references to drive discs are understood to also apply to adaptor discs engaged with the drive discs. Carriage discs may refer to either adaptor discs or drive discs.

The actuator 106 may be a mechanism that actuates the gearbox 108. For example, the actuator 106 may be a motor. In a more particular example, the actuator 106 may be an electric motor such as a brushless motor. The actuator 106 may include a position sensor 120 (e.g., an encoder) that is able to detect the present angular position of the actuator 106. As such, the position sensor 120 can detect the angular position of the gearbox 108 and the drive input 110. And, after successful engagement, the position sensor 120 can sense relative position changes of the input coupling 102, and the joint output 104. The relation between the angular position of both the input coupling 102 and the joint output 104 to the position sensor 120 after successful engagement will be discussed in further detail below.

Within the system 100 illustrated in FIG. 2A, there are a set of known parameters. The known parameters include
- a gear ratio (GR) of the gearbox 108 (a change in drive disc 110 position divided by a change in actuator 106 position);
- a gear ratio (DR) between the instrument disc 102 and the joint output 104 (a change in joint output 104 position divided by a change in instrument disc 102 position);
- a disc offset ($D_{off}$) which is the position of the instrument disc 102 when the joint output 104 position is at a nominal position such that the manipulatable object 114 is in a neutral position. For example, if the joint output 104 is manipulating the pitch of the manipulatable object 114, then the neutral position is the horizontal position illustrated in FIG. 2A;
- a period ($P_{drive-coup}$) between repeating coupling positions. For example, a rotary coupling (e.g., an instrument disc) which engages (e.g., with a drive disc) only once per revolution has a $P_{drive-coup}$ of $2\pi$ radians. If a rotary coupling engages twice per input revolution, $P_{drive-coup} = \pi$ radians;
- a joint output position ($q_{out}$) is constrained by an upper physical constraint 116 with a position ($q_{out\_ul}$) and a lower physical constraint 118 ($q_{out\_ll}$).

Using the position of the actuator 106 as determined by the position sensor 120, the position of other components can be determined as well. The equations governing engagement between the drive disc 110 and the instrument disc 102 include:
- the position of the drive disc 110: $d_{sens} = GR \times m_{sens}$ where, $m_{sens}$ is the sensed position of the actuator 106;
- the offset applied to the position of the drive disc 110 to create the correct mapping between the drive disc 110 and the manipulatable object 114 at joint output $q_{out}$: $d_{coup\_offset} = D_{off} + n \times P_{drive-coup}$, where n = a positive or negative integer;
- the position of the instrument disc 102: $d_{coup} = d_{sens} + d_{coup\_offset}$;
- position of the joint output 104: $q_{out} = DR \times d_{coup}$.

In this embodiment changing the pitch moves the manipulatable object 114 towards the upper physical constraint 116 or the lower physical constraint 118. However for other types of movement, the physical constraint may have a different configuration (see. FIGS. 5A and 5B for physical constraint with roll movement).

When engaging the drive disc 110 to the instrument disc 102, it is not necessarily known when or if the drive disc 110 has successfully engaged the instrument disc 102. According to principles described herein, the actuating element 103 rotates far enough to cover all position uncertainty of the instrument disc 102 and to reach a target output joint constraint 116, 118. If a resistance torque is experienced by the actuator 106, and that resistance torque is greater than a predefined torque threshold, then it is known that the manipulatable object 114 has reached either the upper physical constraint 116 or the lower physical constraint 118, thus indicating that the drive disc 110 has been successfully engaged to move the manipulatable object 114. If, after the commanded engagement motion of the drive input is completed, no such resistance torque is experienced (i.e., the torque threshold has not been met), then it can be determined that the drive disc 110 has not successfully engaged. More specifically, if the absolute value of the torque at the joint output 104 when motion is stalled by the physical constraint ($|\tau_{joint}|$) is greater or equal to the threshold torque, $\tau_{thresh}$, then engagement has been successful, otherwise engagement has failed.

The torque threshold is chosen to be greater than the maximum expected inherent resistance torque of all of the components of the drive train. The drive train torque resistance may be affected by the various components described in FIG. 2A. For example, the position sensor 120, motor actuator 106, gearbox 108, drive input 110 to input coupling 102 interface, input coupling 102 to drive belt 112 interface, and drive belt 112 to joint output 104 interface may all contribute to the drive train torque resistance. Additionally, the torque threshold is chosen to be less than the maximum torque at the drive input 110.

As the determination of successful engagement occurs at a static stalled position, the joint output torque is related to the position error as $|\tau_{joint}|=K_p*|e_{joint}|$, where Kp is a torsion constant of the joint output. Therefore, the final commanded position of the engagement motion can be chosen to be at least $|e_{joint}|=\tau_{thresh}/K_p$, beyond the joint output constraint that is targeted, plus any additional motion needed at the drive input 110 needed to cover the position uncertainty of the input coupling 102, and any compliance in the drive train.

One example for $\tau_{thresh}$ is the average of the inherent resistance torque of the drive train and the maximum torque at the drive input. For example, if the maximum inherent resistance torque of the drive train is 0.1 Nm and the configured maximum torque at the drive input is 0.3 Nm, then $\tau_{thresh}$ may be 0.2 Nm. This, in turn, means that the commanded motion of the drive input needs to go beyond the position uncertainty, joint output constraint and drive-train compliance by at least 0.2 Nm/$K_p$. If, for example, $K_p$=5.0 Nm/rad, then the commanded motion needs to be at least 0.2 Nm/5.0 Nm/rad=0.04 rad greater than the maximum possible motion required for engagement.

After it is determined that engagement is successful, then the position of the actuator 106, as determined by the position sensor 120, can be mapped to the position of the joint output 104. This is important because it may be the case that the drive disc 110 made several rotations before engaging. Or, if the drive disc 110 can engage the instrument disc 102 at multiple locations within a single revolution, it may not be known at which location engagement has occurred. Thus, $d_{coup\_offset}$, which is the offset applied to the position of the drive disc 110 to create the correct mapping between the drive disc 110 and the manipulatable object 114 at joint output $q_{out}$ can be determined by identifying the integer n in the equation $d_{coup\_offset}=D_{off}$-n×$P_{drive-coup}$. The integer n is defined as "n"=Round $(((q_{out\_ul}/DR)-d_{sens}-D_{off})/(P_{drive-coup}))$, when driving to the upper constraint 116 of the joint output range or as "n"=Round $(((q_{out\_ll}/DR)-d_{sens}-D_{off})/(P_{drive-coup}))$, when driving to the lower constraint 118 of the joint output range.

By mapping the position of the actuator with the position of the joint output, the control system that moves the manipulatable object can accurately determine the position of the manipulatable object based on the position of the actuator 106. Thus, in the example where the manipulatable object is a medical instrument attached to a teleoperative manipulator arm. The control system can accurately control the medical instrument during a surgical operation.

Figure 2B:
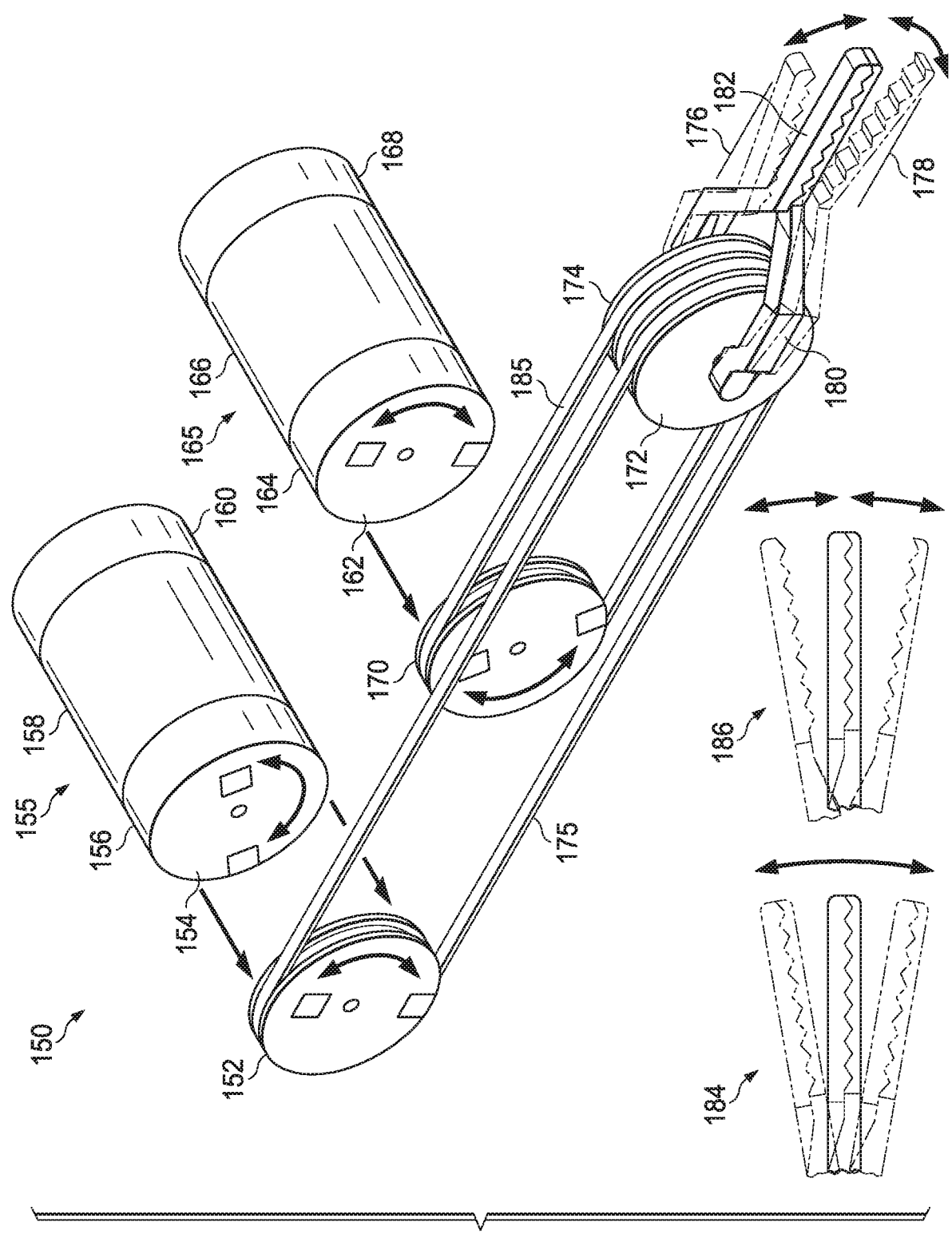
FIG. 2B is a diagram showing an illustrative system for engaging multiple drive discs to multiple instrument discs that are coupled to joint outputs, according to one example of principles described herein.

FIG. 2B is a diagram showing an illustrative system for engaging multiple drive discs 154, 162 (e.g., drive discs of the carriage 60) to multiple instrument discs that are coupled to multiple joint outputs 172, 174 (e.g., the wrist joint 68). In some cases, more than one drive disc may be used to drive an instrument in a particular manner. For example, in a two fingered instrument, one drive disc may drive one finger while a second drive disc drives the other finger. Thus, to change the pitch of the instrument tip, both drive discs must act in coordination with each other to move the instrument tip accordingly.

According to the present example, a first actuating element 155 includes a first actuator 158, a first gearbox 156, and a first drive disc 154. The first actuator 158 is connected to the first gearbox 156. The first gearbox 156 is coupled with the first drive disc 154. The first drive disc 154 is configured to engage a first instrument disk 152. The first instrument disc 152 is coupled to a first joint output 172 through a first actuation system 175. The joint output may be connected to a manipulatable object 180 such as a first finger. While the system 175 is illustrated as a pulley, the system 175 may be a set of gears, cables, drive rods, or other actuating members coupling the instrument disc 152 to the joint output 172.

Additionally, a second actuating element 165 includes a second actuator 166, a second gearbox 164, and a second drive disc 162. The second actuator 166 is connected to the second gearbox 164. The second gearbox 164 is coupled with the second drive disc 162. The second drive disc 162 is configured to engage a second instrument disk 170. The second instrument disc 170 is coupled to a second joint output 174 through a second actuation system 185. The second joint output 174 is connected to a second manipulatable object 182 such as a second finger. While the system 185 is illustrated as a pulley, the system 185 may be a set of gears, cables, drive rods, or other actuating members coupling the instrument disc 170 to the joint output 174.

The joint outputs 172, 174 are configured to move the manipulatable objects 180, 182 (e.g., the tip 66). For example, when both joint outputs 172, 174 move in the same direction, the pitch (or yaw) of the manipulatable objects 180, 182 will change. If, however, the joint outputs 172, 174 move in opposite directions, the fingers 180, 182 will open or close, thus adjusting the grip of the instrument.

While only two input discs are illustrated in FIG. 2B, various embodiments may include several drive discs to move an instrument in various degrees of freedom. Generally, one or more drive discs may engage one or more instrument discs coupled to one or more joint outputs. It is desirable to confirm engagement of each of these discs before operation of the instrument. It is also desirable to determine the proper mapping from the drive discs to the joint output for all joint outputs that are controlled.

Within the system 150 illustrated in FIG. 2B, there are a set of known parameters. The known parameters include
a gear ratio ($GR_j$) of the jth gearbox (a change in drive disc position divided by a change in actuator position);
a gear ratio ($DR_{ij}$) between the jth instrument disc and the ith joint output (a change in joint output position divided by a change in instrument disc position);
a disc offset ($D_{offj}$) which is the position of the jth instrument disc when all joint outputs are in a neutral position within the multiple degrees of freedom.
a period ($P_{drive-coupj}$) between repeating coupling positions of the jth interface.
a position ($q_{outi}$) of the ith joint output, which is constrained by an upper physical constraint 176 with a position ($q_{out\_ulj}$) and a lower physical constraint 178 ($q_{out\_llj}$).

Additionally, a coupling matrix ($C_{DR}$) may be used to represent the relation between all of the drive disks and all of the joint outputs. For example:

$$C_{DR} = \begin{bmatrix} DR_{11} & \cdots & DR_{1N} \\ \vdots & \ddots & \vdots \\ DR_{M1} & \cdots & DR_{MN} \end{bmatrix}$$

Using the position of the actuators 158, 166 as determined by the respective position sensors 160, 168 the position of other components can be determined as well. The equations governing engagement between the drive discs and the instrument discs include:
the position of the jth drive disc: $d_{sensj}=GR_j \times m_{sensj}$ where, $m_{sensj}$ is the sensed position of the jth actuator;
the offset applied to the position of the jth drive disc to create the correct mapping between the jth drive discs and the joint outputs $q_{out}$: $d_{coup\_offsetj}=D_{offj}+k_j \times P_{drive-coupj}$, where $k_j$=a positive or negative integer;
the position of the jth instrument disc: $d_{coupj}=d_{sensj}+d_{coup\_offsetj}$;
position of the ith joint output: [$q_{out}$] (an m×1 matrix of the i joint outputs)=$C_{DR}\times[d_{coup}]$ (an n×1 matrix of the j instrument disks).

For a set of drive discs, each drive disc is driven a configurable distance intended to reach the joint output constraints 176, 178 until motion of all the discs stops. When motion has stopped it can be determined for each disc whether engagement has occurred successfully based on the torque resistance experienced by that disc. When using multiple degrees of freedom, the torque resistance can be measured from the torque resistance experienced by the drive discs 154, 162.

For example, if the absolute value of the torque at the drive discs after motion has stalled ($|\tau_{drive\_inputj}|$) is greater than a torque threshold ($\tau_{engage\_threshj}$), then it is known that engagement has occurred successfully. Otherwise, engagement is not confirmed and the instrument may have to be reinstalled.

After it is determined that engagement is successful for each of the drive disks 154, 162, then the position of the actuators 158, 166, as determined by the position sensors 160, 168, can be mapped to the position of the joint outputs 172, 174. This is important because it may be the case that the drive disks 154, 162 made several rotations before engaging. Or, if the drive discs 154, 162 can engage the instrument discs 152, 170 at multiple locations within a single revolution, it may not be known at which location engagement has occurred. Thus, the offset applied to the position of the jth drive disc to create the correct mapping between the jth drive disc and the corresponding joint output can be determined by solving the following equation:

$$[D_{neg\_ext}]=[C_{DR}^{-1}][q_{out-lim}]-[d_{sens}]-[D_{off}].$$

[$D_{neg\_ext}$] is the [m×1] vector of the negative of the extra motion at the drive disks to reach the joint output constraints. [$C_{DR}^{-1}$] is the inverse of coupling matrix $C_{DR}$ (a suitable pseudo-inverse may also be used). [$q_{out-lim}$] is the [m×1] vector of joint output constraints that were targeted. This vector can have a configurable combination of upper, lower, and no limits that are consistent with the drive disk engagement, In other words, the set of joints for which limits are configured may span the drive inputs that will be engaged (as indicated in the $C_{DR}$ matrix). [$d_{sens}$] is the [m×1] vector of sensed position of the drive disks. [$D_{off}$] is the [m×1] vector of the disk offsets. The extra periods (Rj) for each of the engagements may thus be defined as $Rj=ROUND(D_{neg\_extj}-P_{drive-coupj})$.

Figure 2C:
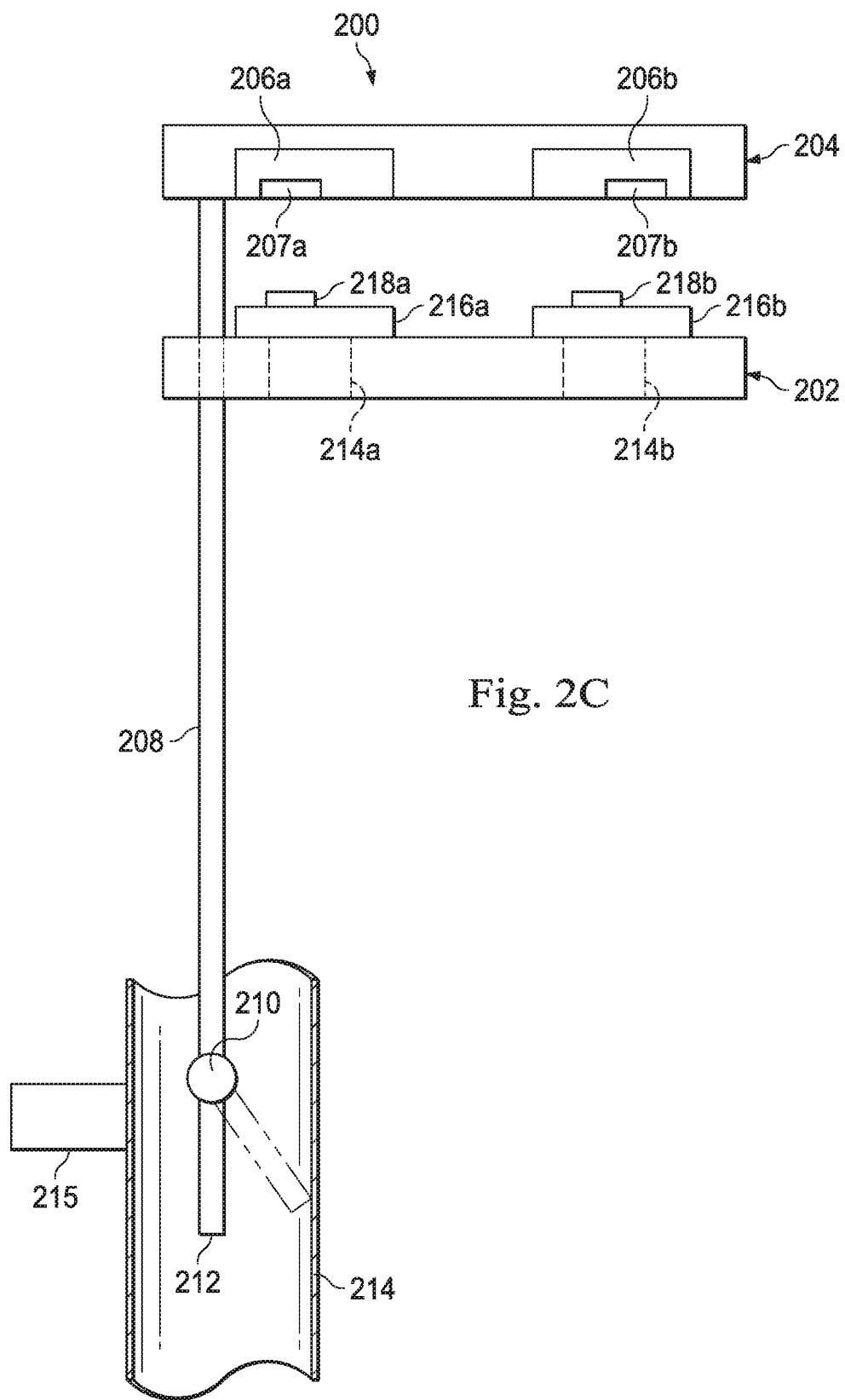
FIG. 2C is a diagram showing illustrative engagement of an instrument disc with a drive disc, according to one example of principles described herein.

FIG. 2C illustrates the engagement between an instrument 200 which may be substantially the same as instrument 59 and an instrument carriage 202 which may be substantially the same as instrument carriage 60. These components may be engaged utilizing the principles described above in the text accompanying FIG. 2A. An instrument body 204 of the instrument 200 includes instrument discs 206a, 206b. Each instrument disc 206a, 206b includes a pocket 207a, 207b, respectively. In some examples, there may be more than one pocket in the drive disc. For example, there may be two bosses at 180 degrees from each other. The instrument 200 further includes an instrument shaft 208 extending from the instrument body 204, a wrist joint 210, and an actuatable tip 212. Actuating members (not shown) extend through the shaft 208 to couple the instrument discs 206a, 206b to the wrist joint 210 and the tip 212. A cannula 214 is coupled to a distal end of an instrument spar 215 and is sized to receive the shaft 208, wrist joint 210, and tip 212. The instrument carriage 202 houses motors 214a, 214b for driving movement of drive discs 216a, 216b, respectively. In this embodiment, the motors 214a and 214b may be used in coordination to generate either a pitch motion or a yaw motion or a combination of pitch and yaw motion in the actuatable tip 212.

Each of the drive discs 216a, 216b includes a boss 218a, 218b, respectively. The bosses 218a, 218b may be positioned near the circumference of the discs 216a, 216b. In some examples, there may be more than one boss on the drive disc. For example, there may be two bosses at 180 degrees from each other. For simplicity, a sterile adaptor (e.g., adaptor 74) has been omitted from this embodiment. In various other embodiments, as shown in FIG. 1E above, a sterile adaptor including adaptor discs is couplable between the drive disc and the corresponding instrument disc. In these alternative embodiments, the instrument discs engage with adaptor discs that are directly mated to and rotationally synchronized with the drive discs. In various other embodiments, the boss and pocket configuration may be switched with the boss protruding from the instrument disc and a pocket in the drive disc.

The boss 218a on the drive disc 216a is designed to engage with the corresponding pocket 207a on the instrument disc 206a. The boss 218b on the drive disc 216b is designed to engage with the corresponding pocket 207b on the instrument disc 206b. If the drive disc includes multiple bosses, then the instrument disc will include multiple corresponding pockets. When the drive discs 216a, 216b are first placed adjacent to the instrument discs 206a, 206b, it is not likely that each set of discs 216a, 206a and 216b, 206b will be aligned to the proper rotational positions such that the bosses will slide into the pockets. Rather, the motor coupled to each drive disc will cause the instrument disc to rotate until the boss slides into the pocket. Before the boss engages the pocket, rotation of the drive disc 206 does not necessarily cause rotation of the instrument disc.

In one example, the drive discs 216a, 216b correspond to the drive discs 154, 162 of FIG. 2B. Thus, the drive discs 216a, 216b may be used in coordination to drive the instrument tip 212 in multiple degrees of freedom. When multiple sets of drive and instrument discs are present, possibly one or more of the disc sets may fail to engage.

After the boss 218a successfully engages the pocket 207a, rotation of the drive disc 216a will cause rotation of the instrument disc 206a. Each instrument disc is coupled with a particular movement of the instrument 200. For example, rotation of one or more instrument discs may cause a change in pitch, yaw, or roll or some combination thereof of the tip 212. If the tip 212 includes a gripping member, the rotation of a set of the instrument discs may control a change in grip.

In one example, in order to determine whether the boss 218a of the drive disc 216a has successfully engaged the pocket 207a of the instrument disc 206a, the instrument is inserted into a position where a pitch movement of the wrist 210 will cause the actuatable tip 212 to touch the physical limitation of the inside wall of the cannula 214. After the instrument 200 is positioned as described with the actuatable tip 212 in the cannula 214, the motor coupled to the drive disc 216a applies a rotational force until a resistance torque is experienced. If a resistance torque is experienced, it is known that the drive disc 216a, responsible for pitch motion of the actuatable tip 212, has properly engaged with the instrument disc 206a. Specifically, if both discs 206a, 216a have successfully engaged, then rotation of the drive disc 216a will cause rotation of the instrument disc 206a, which in turn, will cause pitch movement of the actuatable tip 212. Such movement will eventually lead the actuatable tip 212 to reach the physical limitation of the wall of the cannula 214. Similarly, the engagement of the boss 218b of the drive disc 216b with the pocket 207b of the instrument disc 206b may be confirmed by applying a rotational force from the motor 214b to the drive disc 216b. If the actuatable tip 212 contacts the wall of the cannula 214 in a yaw motion, the motor 214b experiences a resistance torque and proper engagement of the drive disc 216b with the instrument disc 206b is confirmed. In some cases, such as when multiple drive discs map to one or more joint outputs, proper engagement and mapping is coordinated as described above in the text corresponding to FIG. 2B.

The process of disc engagement confirmation may continue for each motor of the instrument carriage 202. Some disc engagement confirmation procedures may not require the cannula 214 to provide the physical limitation. For example, the engagement confirmation process for a motor controlling instrument roll, as described in greater detail in FIGS. 4A, 4B, utilizes a stopping mechanism on the discs. For two-piece gripping instruments, each piece may act as a physical limitation to the other. For example, actuating one piece to move in an opposite yaw direction from the other piece will cause the two-pieces to collide, thus providing a physical limitation and confirmation of disc engagement to the motors driving each yaw movement. After a resistance torque is experienced by each of the motors that drive the drive discs, a control system for the teleoperative medical system may know that engagement has been successful. The medical procedure may then proceed accordingly. But, if the resistance torque is not experienced by each of the motors necessary for driving the instrument joint outputs, then it can be determined that the engagement has not been successful. An operator may then be notified and instructed to remove and reconnect the instrument to the instrument carriage. The system may also prevent further action with the instrument. For example, axial insertion of the actuatable tip beyond the cannula may be prevented.

Figure 3:
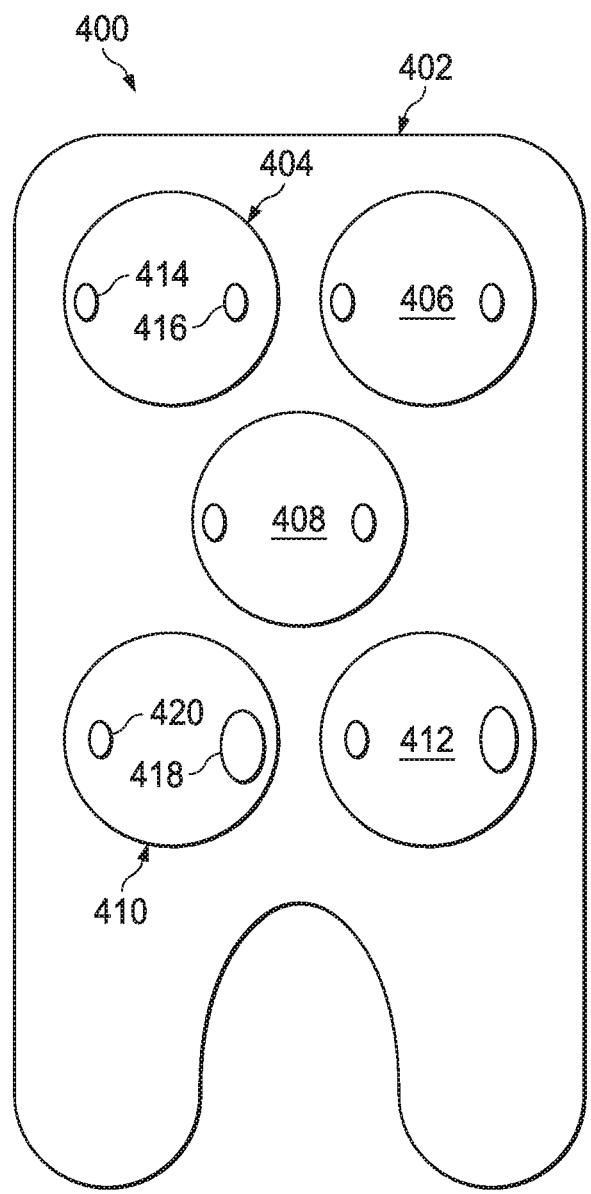
FIG. 3 is a diagram showing an illustrative carriage to connect an instrument to a manipulator arm of a teleoperative medical system, according to one example of principles described herein.

FIG. 3 is a diagram 400 showing an illustrative carriage 402 with multiple drive discs 404, 406, 408, 410. In this example, the adaptor carriage 402 includes five discs. An instrument may be designed to use any number of the discs. For example, one instrument may use only three of the discs. Another instrument may use all five discs.

In the present example, each of the discs includes two bosses positioned at 180 degrees from each other. Additionally, the two bosses on the same disc are different enough from each other so that the disc will only engage a corresponding instrument disc at one angular position. For example, the first three discs 404, 406 408 have the bosses positioned such that one boss 414 is closer to the circumference of the disc than the other boss 416 (e.g., boss 414 is closer to the edge of the disc 404 than boss 416 is). Thus, the bosses 414, 416 will only engage the corresponding pockets of a corresponding instrument disc at one angular position within 360 degrees of rotation. The fourth and fifth discs 410, 412, have bosses structured so that one boss 418 is larger than the other boss 420. Thus, the bosses 418, 420 will only engage the corresponding pockets of the instrument disc at one angular position within 360 degrees of rotation.

The different discs may be used for different types of movement. For example, the first disc 404 may be used to control the roll of the instrument about the instrument's axis. The third disc 408 may be used to control the pitch of the instrument. A coordinated motion of the third, fourth and fifth discs (408, 410, 412) may be used to control the yaw of the instrument. A different coordinated motion of the fourth disc 410 and fifth disc 412 may be used to control grip of the instrument. Each of these discs can be checked for proper engagement using the principles described above. Specifically, each disc is rotated until the motor driving the disc experiences a resistance torque.

Figure 4A:
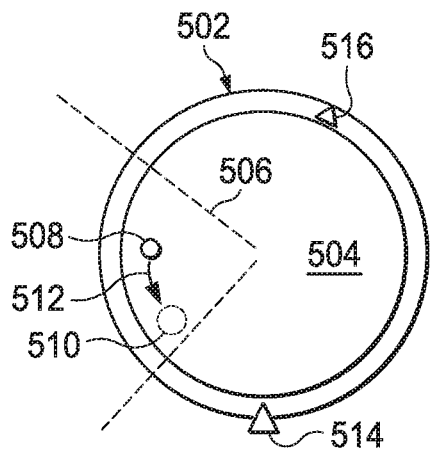
FIGS. 4A-4H are diagrams showing illustrative top view of disc engagement, according to one example of principles described herein.
Figure 4B:
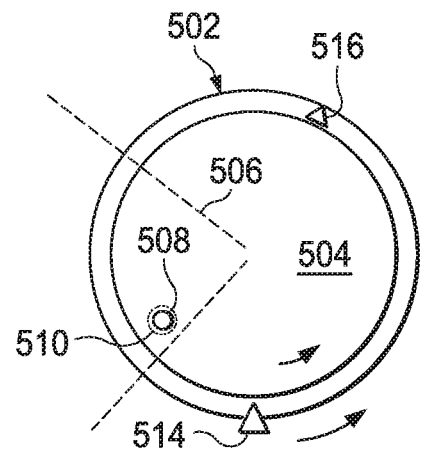
Figure 4C:
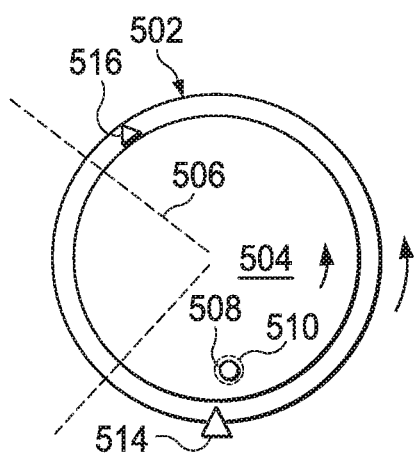
Figure 4D:
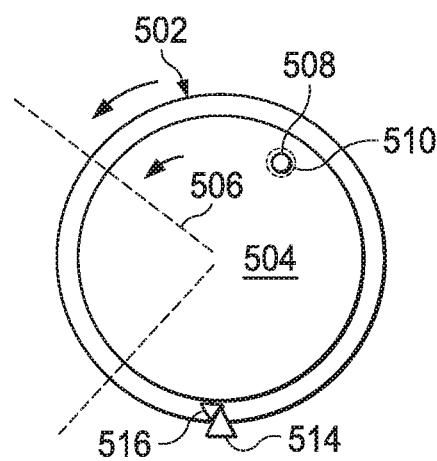

FIGS. 4A-4D are diagrams showing illustrative top views of disc engagement for a roll actuator. According to the present example, a drive disc 504 (or a mated adaptor disc if a sterile adaptor is used) includes a boss 508. An instrument disc 502 is placed adjacent to the drive disc 504. The instrument disc 502 includes a pocket 510. In this example, the discs 502, 504 are used to drive the roll of an instrument. Because an instrument may continuously roll without experiencing a physical limitation, an external hard stop provides that limitation. Specifically, the instrument disc 502 includes a protrusion 516. A protruding stopping mechanism 514 along the rotational travel path of the protrusion 516 provides a physical limitation or hard stop when the protrusion is rotated into abutment with the stopping mechanism. As shown in FIG. 4A, when the instrument disc 502 is first placed against the drive disc 504, the boss 508 is not necessarily aligned with the pocket 510. In some examples, the possible initial position of the pocket 510 may be within a specific range of variability 506. In the initial configuration of FIG. 4A, the drive disc 504 may begin to rotate 512 counter-clockwise such that the boss 508 will move toward the stationary pocket 510. As shown in FIG. 4B, when the rotation of the drive disc 504 brings the boss 508 over the pocket 510, the boss may be received into the pocket. In some embodiments, the boss or the pocket may be biased, for example by a spring, to influence the boss to engage the pocket. As shown in FIG. 4C, after the boss 508 is engaged with the pocket 510, the continued rotation of the drive disc 504 causes the instrument disc 502 to rotate with the drive disc 504. As the instrument disc 502 rotates, the protrusion 516 also rotates. Continued rotation of the instrument disc 502 and drive disc 504 brings the protrusion 516 into abutment with the stopping mechanism 514, as shown in FIG. 4D. At this position, the motor driving the drive disc 504 will experience a resistance torque. This indicates that the boss 508 has successfully engaged the pocket 510. With the initial arrangement of the boss 508 and pocket 510 as shown in FIG. 4A, the drive disc 504 will rotate less than 360° before the protrusion 516 and the stopping mechanism prevent further rotation of the drive disc.

Figure 4E:
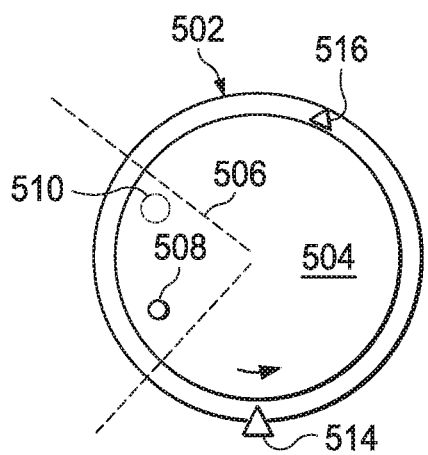
Figure 4F:
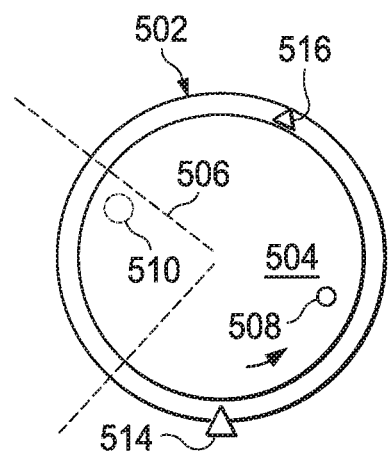
Figure 4G:
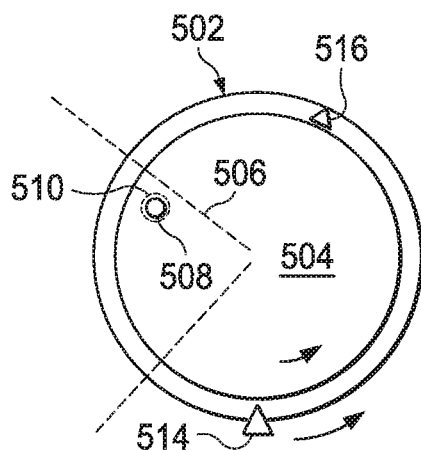
Figure 4H:
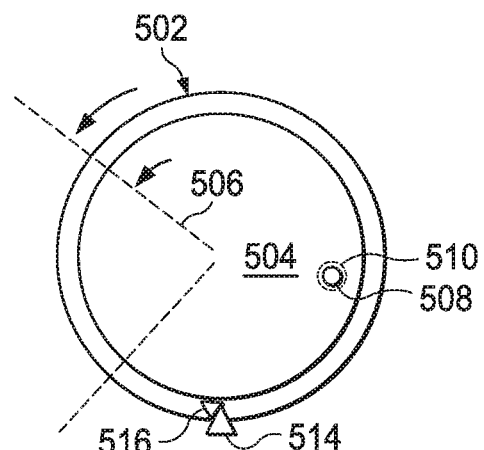

With an initial configuration of the boss 508 and pocket 510 as shown in FIG. 4E, the drive disc 504 will rotate more than 360° before the protrusion 516 and the stopping mechanism prevent further rotation of the drive disc. As shown in FIG. 4E, when the instrument disc 502 is first placed against the drive disc 504, the boss 508 is not necessarily aligned with the pocket 510. As shown in FIG. 4F, the boss 508 must travel nearly an entire rotation before engaging the boss 510. As shown in FIG. 4G, when the rotation of the drive disc 504 brings the boss 508 over the pocket 510, the boss may be received into the pocket. In some embodiments, the boss or the pocket may be biased, for example by a spring, to influence the boss to engage the pocket. As shown in FIG. 4H, continued rotation of the instrument disc 502 and drive disc 504 brings the protrusion 516 into abutment with the stopping mechanism 514. At this position, the motor driving the drive disc 504 will experience a resistance torque. This indicates that the boss 508 has successfully engaged the pocket 510. With the initial arrangement of the boss 508 and pocket 510 as shown in FIG. 4E, the drive disc 504 will rotate more than 360° before the protrusion 516 and the stopping mechanism prevent further rotation of the drive disc. In some cases, the drive disc 504 may make several full turns before successfully engaging the pocket 510. The number of turns before engagement may be recorded and used to map the position of the motor with the position of the instrument coupled to the instrument disc 502.

Figure 5:
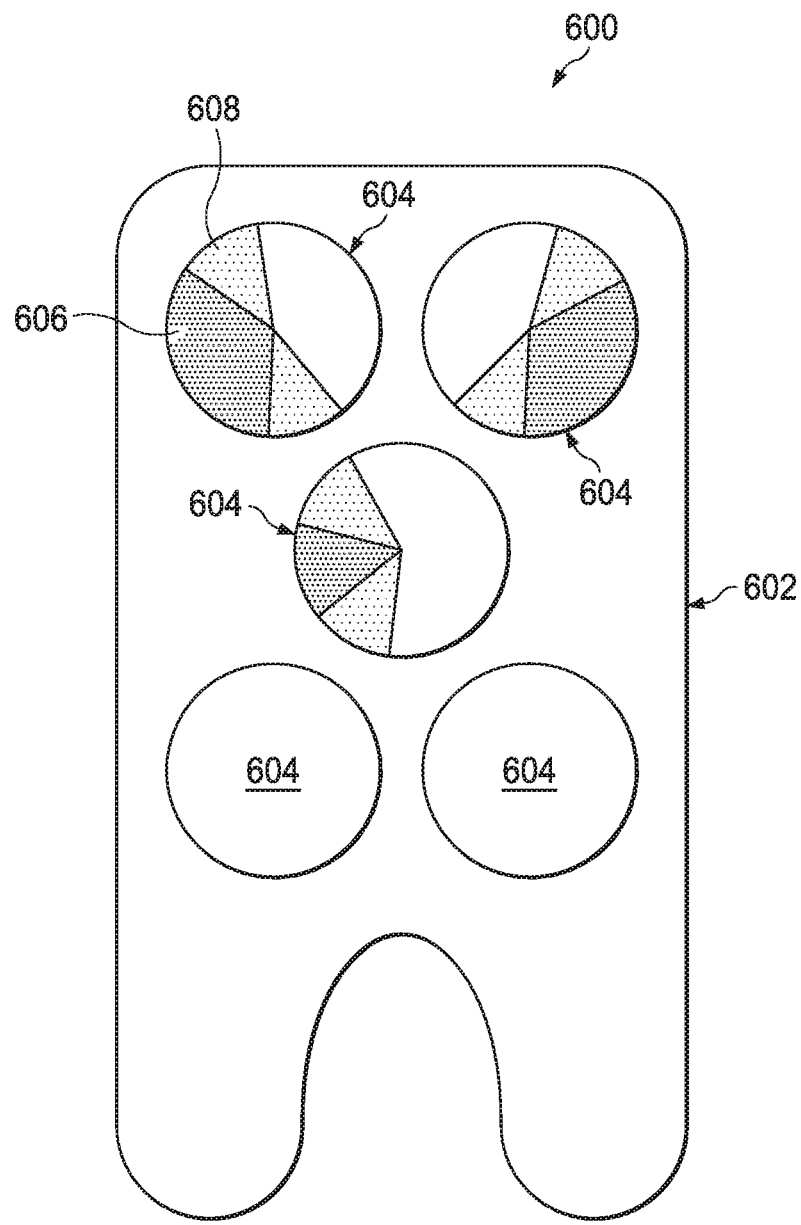
FIG. 5 is a diagram showing initial disc position variability, according to one example of principles described herein.

FIG. 5 is a diagram 600 showing initial disc position variability. According to the present example, an instrument carriage 602 includes five different discs 604. The initial disc position range may be defined by pose variability 606 and offset variability 606.

The pose variability 606 indicates the possible range of poses in which the instrument coupled to the disc 604 may be positioned, with respect to the degree of freedom associated with the disc 604. Specifically, when the instrument carriage 602 is first engaged with the adaptor, the instrument may not be in a neutral position with respect to each degree of freedom. Rather, there may be a range of positions in which the instrument may be placed, thus causing a range in initial disc position. The disc offset variability may be caused by variability due to part tolerances in the instrument drive trains.

Additionally, the initial position of the instrument discs 604 may be subject to a disc offset 608. As described above, the disc offset 608 is the position of the disc when the instrument is at a neutral position, with respect to the associated degree of freedom. For example, when the pitch is at a neutral position, the angular position of the disc may be offset from the nominal zero angular position due to various characteristics of the drive system that couples the instrument disc 604 to the instrument. For example, in some cases, such as with use of cable driven joint outputs, the disc offset may be given a range of about 120 degrees.

Figure 6:
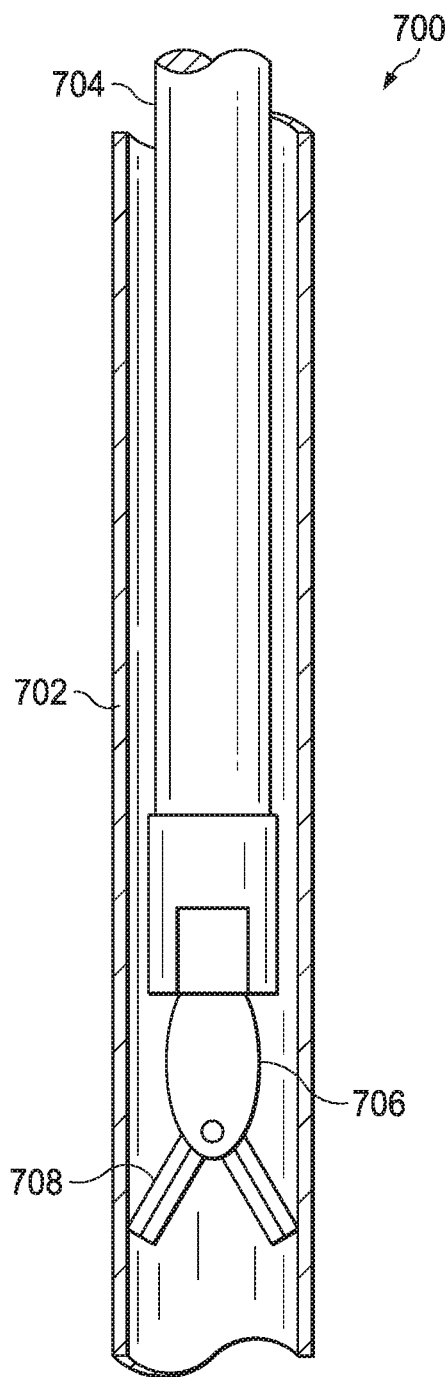
FIG. 6 is a diagram showing an illustrative gripping tool within a cannula, according to one example of principles described herein.

FIG. 6 is a diagram showing an illustrative gripping tool 704 within a cannula 702. According to the present example, two discs within a carriage may be used to drive the grip on a two-fingered instrument such as a gripping tool 704. The gripping tool 704 may experience two physical limitations. One physical limitation corresponds to the gripping tool being closed such that both fingers 708 are closed against each other. When the two fingers 708 are closed against each other, the motors driving the discs associated with the grip may experience a resistance torque, thus indicating successful engagement. Another physical limitation is when the two fingers 708 are opened up against an obstruction such as the inner wall of a cannula 702. Thus, when the instrument fingers 708 are opened as wide as possible within the cannula 702, the motors driving the discs associated with the grip will experience a resistance torque, thus indicating successful engagement.

In some cases, multiple discs may be tested simultaneously for engagement. For example, for a two fingered instrument such as the gripping tool 702, various discs may be rotated in a first stage. Specifically, the roll disc may be rotated until a hard stop is reached. Simultaneously, the grip disc can be rotated until the instrument is closed. Also, the pitch and yaw discs may be rotated into a neutral position. During a second stage the pitch discs and the yaw discs are rotated to move the instrument into the side of the cannula. Because there is motion in more than one degree of freedom, the control system can take this into account to determine the proper thresholds at which a resistance torque should be experienced by the appropriate motors.

The engagement stages needed to confirm instrument engagement vary based upon the instrument. The first example is for confirmation of engagement of a single finger, single drive tool. In a first engagement stage, the roll disc may be rotated until a hard stop is reached. Simultaneously, the pitch and yaw discs may be rotated into a neutral position. During a second stage the pitch discs and the yaw discs are rotated to move the instrument into the side of the cannula. Because there is motion in more than one degree of freedom, the control system can take this into account to determine the proper torque thresholds for each motor. At an engagement check stage, the successfulness of the engagement procedure is evaluated. More specifically, the resistance torque experienced by each of the drive inputs is compared to the corresponding torque thresholds. If the engagement check determines that engagement is successful (absolute value of the resistance torque is greater than the torque threshold), the instrument may be moved to an introductory position to begin the medical procedure. If the engagement check determines that the engagement is unsuccessful (position error is less than the position error threshold), the instrument must be reinstalled and the instrument is restricted from entering the surgical workspace. A single-finger, single drive tool includes for example, monopolar cautery hooks/spats.

A second example is for confirmation of engagement of a two finger tool or a delicate one finger double drive tool. In a first engagement stage, the roll disc may be rotated until a hard stop is reached. Simultaneously, the yaw discs (which control grip) may be rotated into a yaw-neutral and grip-closed position. The pitch disk may be rotated to a pitch-neutral position. During a second stage the pitch disc is rotated to move the instrument tip into the side of the cannula. At an engagement check stage, the successfulness of the engagement procedure is evaluated. More specifically, the resistance torque experienced by each of the drive discs is compared to the corresponding torque thresholds. If the engagement check determines that engagement is successful (absolute value of the resistance torque is greater than the torque threshold), then the instrument may be moved to an introductory position to begin a medical procedure. If the engagement check determines that the engagement is unsuccessful (position error is less than the position error threshold), then the instrument may be reinstalled. The instrument may be restricted from entering a surgical workspace until engagement has been confirmed. Examples of two-finger tools and delicate one finger double drive tools include needle drivers, scissors, and snap fit scalpels.

A third example is for confirmation of engagement of clip appliers. In a first engagement stage, the roll disc may be rotated until a hard stop is reached. Simultaneously, the pitch and yaw discs may be rotated into a neutral position. During a second stage the pitch disc is are rotated to move the instrument tip into the side of the cannula. Additionally, the yaw discs are driven to a grip-open position against the cannula. At an engagement check stage, the successfulness of the engagement procedure is evaluated. More specifically, the resistance torque experienced by each of the drive discs is compared to the corresponding torque thresholds. If the engagement check determines that engagement is successful (absolute value of the resistance torque is greater than the torque threshold), then the instrument may be moved to an introductory position to begin the medical procedure. If, however, the engagement check determines that the engagement is unsuccessful (position error is less than the position error threshold), then the instrument may be reinstalled.

A fourth example is for confirmation of instruments with a no-roll hardstop and a double roll drive. In a first engagement stage, both roll drive discs may be rotated in rotationally opposite directions until hard stops are reached. Simultaneously, if grip exists, the grip disc may be driven to the grip-close position. At an engagement check stage, the successfulness of the engagement procedure is evaluated. More specifically, the resistance torque experienced by each of the drive discs is compared to the corresponding torque thresholds. If the engagement check determines that engagement is successful (absolute value of the resistance torque is greater than the torque threshold), then the instrument may be moved to an introductory position to begin the medical procedure. If, however, the engagement check determines that the engagement is unsuccessful (position error is less than the position error threshold), then the instrument may be reinstalled. Examples of instruments with a no-roll hardstop and a double roll drive include camera instruments and curved shears such as HARMONIC ACE® shears available from Ethicon Endo-Surgery, Inc. of Somerville, N.J.

Figure 7:
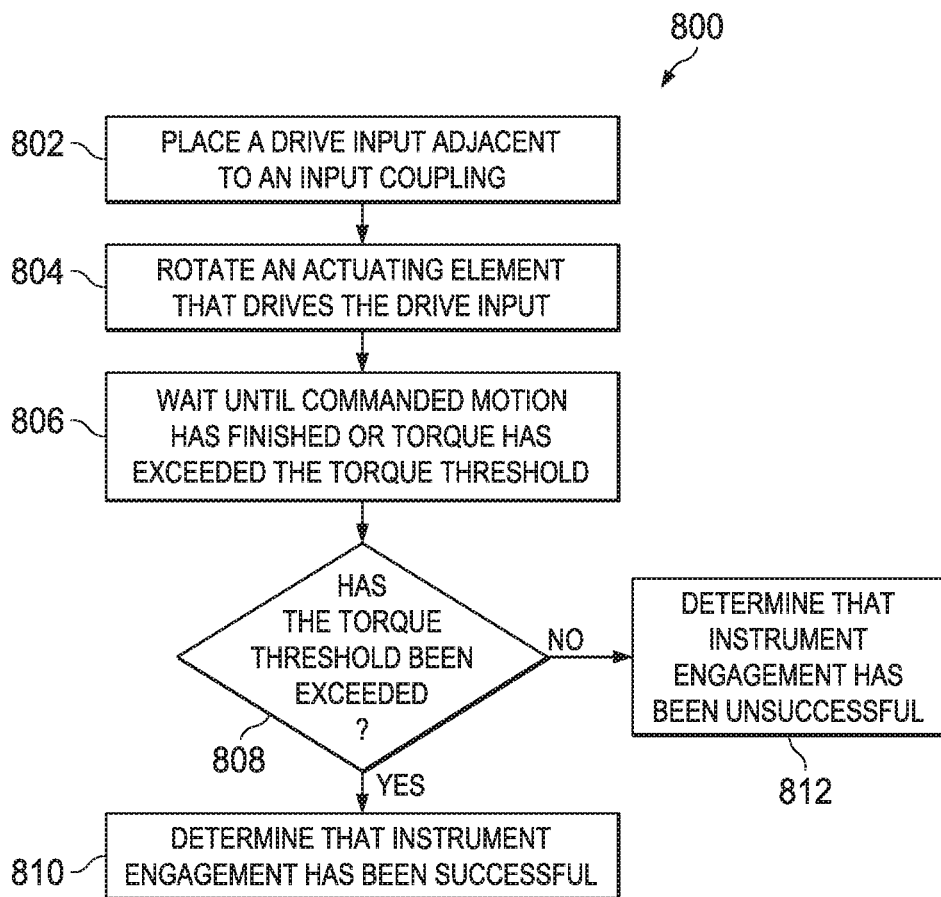
FIG. 7 is a flowchart showing an illustrative method for confirming engagement, according to one example of principles described herein.

FIG. 7 is a flowchart showing an illustrative method for confirming engagement. According to the present example, the method 800 includes a process 802 for placing a drive input (e.g., a drive disc or sterile adaptor disc) adjacent to an input coupling (e.g., an instrument disc). The drive input may be coupled to an actuating element such as a motor. The input coupling may be connected to a joint output through a mechanical system such as a system of gears, pulleys, and other actuating members. The joint output may be secured to a movable object such as an actuatable tip of a medical instrument.

The method 800 further includes a process 804 for rotating the motor that drives the drive input. At process 806 motion continues until it is complete or the motor has experienced a resistance torque greater than the torque threshold. The resistance torque corresponds with a physical limitation of the object secured to the joint output. If a resistance torque is not greater than the specified torque threshold, then, at a process 812 the determination is made that instrument engagement has been unsuccessful. An operator can then be notified and the drive input can be removed and reconnected to the input coupling. Alternatively, the system may autonomously make a second attempt at engagement. If the torque threshold is exceeded, then, at the process 810, a determination can be made that engagement was successful. If engagement has occurred, then a calculation (as described above) may be performed to determine the angular position at which the engagement occurred.

In various embodiments, engagement features may be configured to increase the ease of mating the carriage drive discs and instrument discs or the sterile adaptor discs and the instrument discs. For ease of explanation, the engagement features to couple a carriage 900 (e.g., carriage 202) and an instrument 902 will be described. However, it should be understood that these features may also be used to couple the instrument 902 and a sterile adaptor. In the embodiments discussed below, it will be assumed that the engagement feature of the carriage 900 is configured as a boss and the engagement figure of the instrument 902 is configured as a pocket. However, in another embodiment, the engagement feature of the carriage 900 may be configured as a pocket and the engagement feature of the instrument 902 may be configured as a boss.

Figures 8A, 8B:
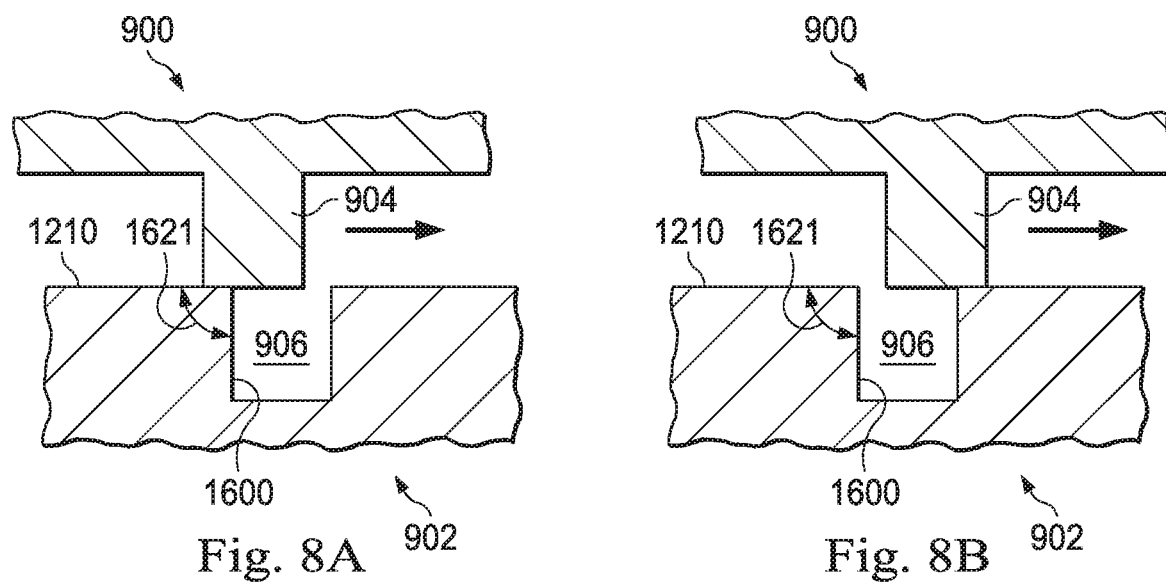
FIG. 8A is an illustration of an exemplary embodiment of an engagement feature of a carriage approaching an instrument engagement feature without an entry ramp.
FIG. 8B is an illustration of the exemplary embodiment of FIG. 8A showing a failed attempt at coupling.

Referring to FIG. 8A, an exemplary illustration of a carriage boss 904 approaching an instrument pocket 906 without an entry ramp is illustrated. It is seen in FIG. 8A that an instrument pocket wall 1600 is at a 90-degree angle 1621 in relation to a surface 1210 of the instrument 902. The boss 904 will insert into the pocket 906 only when the two engagement features are in direct alignment. The size of the protrusion of the boss 904 will correspond almost exactly to the size of the opening of the pocket 906 to decrease the backlash that may arise during rotation after a successful proper engagement. Therefore, it is difficult for the boss 904 to be inserted into the pocket 906, especially when the carriage drivers are rotating at a high speed.

Referring to FIG. 8B, an exemplary illustration of a failed attempt at coupling the boss 904 with the pocket 906 is illustrated. As is seen in FIG. 8B, the boss 904 may bypass the pocket 906, resulting in a failed attempt to couple the two engagement features.

Figure 9A:
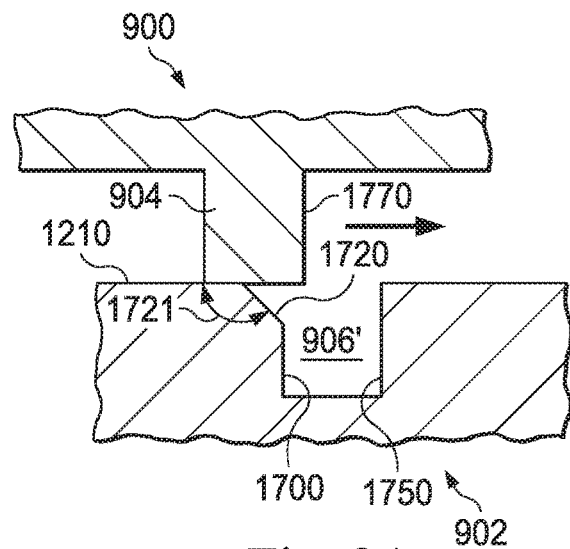
FIG. 9A is an illustration of an exemplary embodiment of an engagement feature of a carriage approaching an instrument engagement feature that includes an entry ramp.

Referring to FIG. 9A, an exemplary illustration of a boss 904 approaching a pocket 906' including an entry ramp 1720 is illustrated. It is seen in FIG. 9A that a wall of the pocket 906' includes an entry ramp 1720 and a straight portion 1700. The entry ramp 1720 is seen to form an obtuse angle of more than 90 degrees in relation to the surface 1210 that supports the boss 904 before it engages the pocket 906'. When the boss 904 approaches the pocket 906', the entry ramp 1720 allows the boss 904 to begin insertion into the carriage pocket 906' before the leading boss wall 1770 reaches the trailing pocket wall 1750.

Figure 9B:
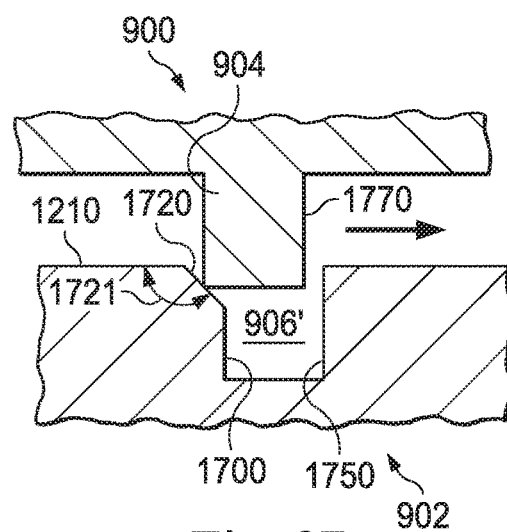
FIG. 9B is an illustration of the exemplary embodiment of FIG. 9A showing the mating of the engagement features.

Referring to FIG. 9B, an exemplary illustration of an boss 904 approaching a carriage pocket 906' and using the entry ramp 1720 to begin insertion into the pocket 906' is shown. When the boss 904 begins sliding down the entry ramp 1720, the boss 904 begins to enter carriage pocket 906'. As the carriage coupler 900 continues to rotate, the leading boss wall 1770 comes in contact with the trailing pocket wall 1750 and the boss 904 is prevented from bypassing the carriage pocket 1221. The spring-loaded mechanism of the carriage driver 900 is then able to propel the insertion of the boss 904 into the pocket 906'. As suggested by FIG. 9B, if the carriage driver 900 contains a spring-loaded mechanism, the carriage driver 900 will rise from the carriage to cause the boss 904 to enter the pocket 906'.

The angle 1721 of entry ramp 1720 in relation to the surface 1210 is only one exemplary embodiment. The angle of the entry ramp may be more than or less than the angle 1721 shown. However, the entry ramp 1720 will always form an obtuse angle with the surface 1210. It will be appreciated that the entry ramp 1720 should be configured so that the straight portion 1700 of the wall of the pocket 906' provides an adequate bearing surface to support the boss 904 when driven against the straight portion of the wall. At a minimum, the straight portion 1700 of the wall needs to be sufficiently high to prevent disengagement when driven in the reverse direction from the direction for engagement.

Figure 10A:
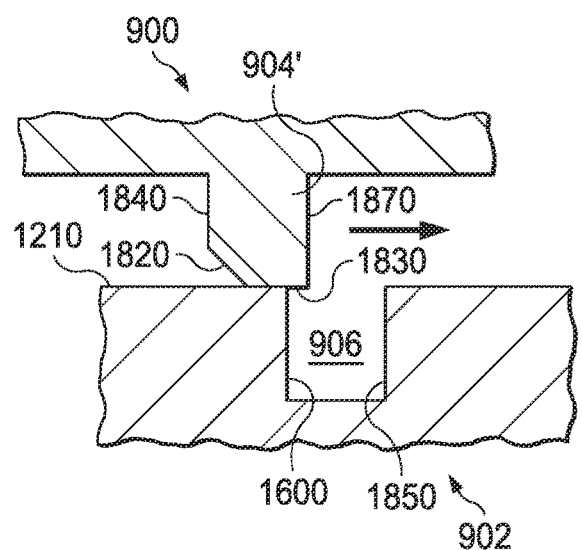
FIG. 10A is an illustration of an exemplary embodiment of an engagement feature of a carriage that includes an entry ramp approaching an instrument engagement feature.

Referring to FIG. 10A, an exemplary illustration of a boss 904' that includes an entry ramp 1820 approaching a pocket 906 is illustrated. It is seen in FIG. 10A that a trailing boss wall 1840 wall includes an entry ramp 1820 that forms an obtuse angle of more than 90 degrees in relation to the lower surface 1830 of the boss 904', the lower surface 1830 supporting the carriage 900 on the surface 1210 of the instrument 902 before it engages the pocket 906.

Figure 10B:
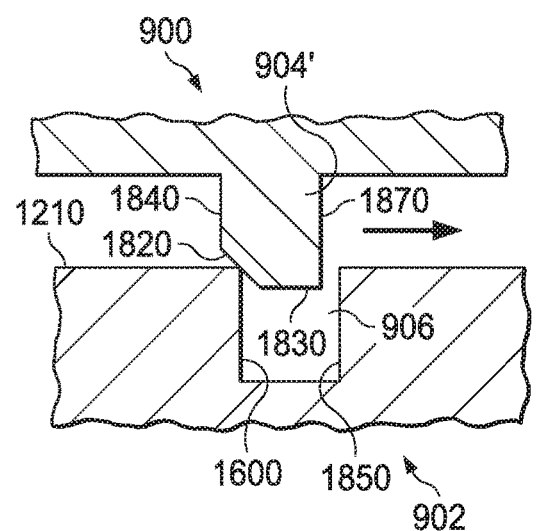
FIG. 10B is an illustration of the exemplary embodiment of FIG. 16A showing the engagement of the mating features.

Referring to FIG. 10B, an exemplary illustration of the boss 904' approaching the pocket 906 and using the entry ramp 1820 to begin insertion into the pocket 906. When the boss 904' approaches the pocket 906, the entry ramp 1820 allows the boss 904' to begin insertion into the pocket 906 before the leading boss wall 1870 reaches the trailing pocket wall 1850. As the carriage 900 continues to rotate, the leading boss wall 1870 comes in contact with the trailing pocket wall 1850 and the boss 904' is prevented from bypassing the pocket 906. The spring-loaded mechanism of the carriage driver 900 is then able to propel the insertion of the boss 904' into the carriage pocket 906. As suggested by FIG. 17B, if the carriage driver 900 contains a spring-loaded mechanism, the carriage driver 900 will rise from the carriage to cause the boss 904' to enter the pocket 906.

The angle of the entry ramp 1820 in relation to the lower surface 1830 of the boss 904' shown is only one exemplary embodiment. The angle of the entry ramp may be more than or less than the angle shown. However, the entry ramp 1820 will always form an obtuse angle with the lower surface 1830 of the boss 904'. It will be appreciated that the entry ramp 1820 should be configured so that the straight portion of the trailing boss wall 1840 wall provides an adequate bearing surface to support the boss 904' when driven against the straight portion of the wall. At a minimum, the straight portion of the trailing boss wall 1840 needs to be sufficiently high to prevent disengagement when driven in the reverse direction from the direction for engagement.

One or more elements in embodiments of the invention may be implemented in software to execute on a processor of a computer system such as a control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy discette, a CD-ROM, an optical disc, a hard disc, or other storage device, the code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
receiving an input coupling adjacent to a drive input, the drive input being driven by an actuating element, the input coupling being coupled to a joint output, the joint output being connected to a movable object;
rotating the actuating element to drive the drive input;
determining, by a control system, whether a resistance torque greater than an inherent drivetrain resistance torque is experienced by the actuating element, wherein the inherent drivetrain resistance torque is for a drivetrain including the input coupling, the drive input, and the joint output; and
determining, by the control system, whether the drive input has engaged the input coupling based on the determination that the resistance torque greater than the inherent drivetrain resistance torque has been experienced by the actuating element.

2. The method of claim 1 wherein determining whether the resistance torque greater than the inherent drivetrain resistance torque of the drivetrain is experienced by the actuating element includes determining whether the resistance torque exceeds a torque threshold.

3. The method of claim 2 wherein the torque threshold is greater than the inherent drivetrain resistance torque and less than a maximum actuating element torque.

4. The method of claim 1 further comprising:
determining an angular position of the actuating element at which the drive input engaged the input coupling.

5. The method of claim 1, wherein the drive input comprises a disc having a boss.

6. The method of claim 5, wherein the input coupling includes an instrument disc, the instrument disc including a pocket corresponding to the boss.

7. The method of claim 6 wherein determining whether the drive input has engaged the input coupling includes determining that the boss is located within the pocket.

8. The method of claim 1, wherein the actuating element comprises a brushless motor.

9. The method of claim 1 wherein rotating the actuating element to drive the drive input includes rotating the actuating element until the movable object encounters a physical limitation.

10. The method of claim 9 wherein the physical limitation is a wall adjacent to the movable object.

11. The method of claim 9 wherein the physical limitation is a rotational stop encountered by the input coupling.

12. The method of claim 1 wherein the joint output includes an instrument wrist and the movable object includes an articulatable instrument tip.

13. The method of claim 1 wherein determining whether the drive input has engaged the input coupling includes determining whether the movable object has moved in a roll motion.

14. The method of claim 1 wherein determining whether the drive input has engaged the input coupling includes determining whether the movable object has moved in a yaw motion.

15. The method of claim 1 wherein determining whether the drive input has engaged the input coupling includes determining whether the movable object has moved in a pitch motion.

16. The method of claim 1 wherein determining whether the drive input has engaged the input coupling includes determining whether two jointed components of the movable object have moved into a closed configuration.

17. A method for confirming instrument engagement, the method comprising:

receiving a plurality of input couplings adjacent to a plurality of drive inputs, wherein each of the plurality of input couplings are configured to cause at least a portion of an instrument to move in at least one degree of freedom, driving the plurality of drive inputs, using a plurality of actuating elements, until movement of the instrument along the at least one degree of freedom has stalled;

determining, by a control system, a resistance torque experienced by each drive input responsible for the movement of the instrument along the at least one degree of freedom that is stalled; and determining, by the control system, whether the drive inputs responsible for the movement of the instrument along the at least one degree of freedom that is stalled have engaged corresponding input couplings based on the resistance torque experienced by each of the drive inputs responsible for the movement of the instrument along the at least one degree of freedom that is stalled.

18. The method of claim 17 further comprising:

mapping positions of the actuating elements to a position of an instrument tip, wherein at least two of the plurality of input couplings coordinate to move the instrument tip along at least one degree of freedom.

19. The method of claim 17 wherein determining the resistance torque experienced by each drive input of the plurality of drive inputs includes at least one of the plurality of drive inputs experiencing the resistance torque when the instrument encounters a physical limitation.

20. The method of claim 17 wherein determining whether the drive inputs responsible for the movement of the instrument along the at least one degree of freedom that is stalled have engaged corresponding input couplings includes determining whether the resistance torque exceeds a threshold torque.

* * * * *